United States Patent
Sawhney

(10) Patent No.: US 7,347,850 B2
(45) Date of Patent: Mar. 25, 2008

(54) ADHESION BARRIERS APPLICABLE BY MINIMALLY INVASIVE SURGERY AND METHODS OF USE THEREOF

(75) Inventor: Amarpreet S. Sawhney, Lexington, MA (US)

(73) Assignee: Incept LLC, Lexington, MA (US)

( * ) Notice: Subject to any disclaimer, the term of this patent is extended or adjusted under 35 U.S.C. 154(b) by 779 days.

(21) Appl. No.: 10/319,308

(22) Filed: Dec. 13, 2002

(65) Prior Publication Data
US 2003/0108511 A1 Jun. 12, 2003

Related U.S. Application Data

(63) Continuation-in-part of application No. 10/010,715, filed on Nov. 9, 2001, now Pat. No. 7,009,034, which is a continuation-in-part of application No. 09/454,900, filed on Dec. 3, 1999, now Pat. No. 6,566,406.

(60) Provisional application No. 60/359,236, filed on Feb. 20, 2002, provisional application No. 60/110,849, filed on Dec. 4, 1998.

(51) Int. Cl.
*A61M 31/00* (2006.01)

(52) U.S. Cl. ................................. 604/500

(58) Field of Classification Search ............ 604/191, 604/82, 83, 197, 240, 500, 506, 507; 424/78, 424/484, 423, 425, 426; 514/772.3
See application file for complete search history.

(56) References Cited

U.S. PATENT DOCUMENTS

| | | | |
|---|---|---|---|
| 3,520,949 A | 7/1970 | Shepard et al. | 260/857 |
| 4,260,077 A | 4/1981 | Schroeder | 222/137 |
| 4,601,286 A | 7/1986 | Kaufman | 128/132 |
| 4,646,730 A | 3/1987 | Schonfeld et al. | 728/156 |
| 4,717,378 A | 1/1988 | Perrault et al. | 604/20 |
| 4,846,405 A | 7/1989 | Zimmermann | |
| 4,902,281 A | 2/1990 | Avoy | 604/191 |
| 4,937,270 A | 6/1990 | Hamilton et al. | 514/777 |
| 5,213,760 A | 5/1993 | Dziabo, Jr. et al. | 422/37 |
| 5,219,564 A | 6/1993 | Zalipsky et al. | 424/78.17 |
| 5,281,662 A | 1/1994 | Ito et al. | 525/54.1 |
| 5,286,258 A | 2/1994 | Haber et al. | 604/90 |
| 5,290,259 A | 3/1994 | Fischer | 604/218 |

(Continued)

FOREIGN PATENT DOCUMENTS

EP 0246380 A2 11/1987

(Continued)

OTHER PUBLICATIONS

L. Mettler et al., A Prospective Clinical Trial of SprayGel™ as a Barrier to Adhesion Formation: Interim Analysis, Department of Obstetrics and Gynecology, University of Kiel, Kiel, GERMANY.

(Continued)

*Primary Examiner*—Nicholas D. Lucchesi
*Assistant Examiner*—Christopher Koharski
(74) *Attorney, Agent, or Firm*—Dardi & Associates, PLLC

(57) ABSTRACT

Biocompatible crosslinked polymers, and methods for their preparation and use with minimally invasive surgery applicators are disclosed. The disclosure includes compositions and methods for in situ formation of hydrogels using minimally invasive surgical techniques.

18 Claims, 12 Drawing Sheets

U.S. PATENT DOCUMENTS

| | | | | |
|---|---|---|---|---|
| 5,296,518 | A | 3/1994 | Grasel et al. | 521/176 |
| 5,322,510 | A | 6/1994 | Lindner et al. | 604/82 |
| 5,368,563 | A | 11/1994 | Lonneman et al. | 604/82 |
| 5,410,016 | A * | 4/1995 | Hubbell et al. | 528/354 |
| 5,419,491 | A | 5/1995 | Breitsprecher | 239/9 |
| 5,423,821 | A | 6/1995 | Pasque | 606/74 |
| 5,431,639 | A | 7/1995 | Shaw | 604/264 |
| 5,474,540 | A | 12/1995 | Miller et al. | 604/191 |
| 5,514,379 | A | 5/1996 | Weissleder et al. | 424/426 |
| 5,527,856 | A | 6/1996 | Rhee et al. | 525/54.1 |
| 5,529,914 | A | 6/1996 | Hubbell et al. | 435/182 |
| 5,550,188 | A | 8/1996 | Rhee et al. | 525/54.1 |
| 5,573,934 | A | 11/1996 | Hubbell et al. | 435/177 |
| 5,580,923 | A | 12/1996 | Yeung et al. | 525/54.1 |
| 5,582,596 | A | 12/1996 | Fukunaga et al. | |
| 5,605,541 | A | 2/1997 | Holm | 604/82 |
| 5,612,052 | A | 3/1997 | Shalaby | 424/426 |
| 5,656,035 | A | 8/1997 | Avoy | 604/191 |
| 5,672,662 | A | 9/1997 | Harris et al. | 525/408 |
| 5,681,576 | A | 10/1997 | Henry | 424/426 |
| 5,702,361 | A | 12/1997 | Evans et al. | 604/53 |
| 5,722,950 | A | 3/1998 | Fujita et al. | 604/48 |
| 5,740,965 | A | 4/1998 | Miyagi et al. | |
| 5,744,545 | A | 4/1998 | Rhee et al. | 525/54.1 |
| 5,752,974 | A | 5/1998 | Rhee et al. | 606/214 |
| 5,759,169 | A | 6/1998 | Marx | |
| 5,773,025 | A | 6/1998 | Baichwal | 424/458 |
| 5,776,493 | A | 7/1998 | Barclay et al. | 424/468 |
| 5,786,421 | A | 7/1998 | Rhee et al. | 525/54.1 |
| 5,800,541 | A | 9/1998 | Rhee et al. | 623/11 |
| 5,801,033 | A | 9/1998 | Hubbell et al. | 435/182 |
| 5,830,178 | A | 11/1998 | Jones et al. | 604/49 |
| 5,830,196 | A | 11/1998 | Hicks | 604/280 |
| 5,844,023 | A | 12/1998 | Tomka | 524/47 |
| 5,869,096 | A | 2/1999 | Barclay et al. | 424/468 |
| 5,874,500 | A * | 2/1999 | Rhee et al. | 525/54.1 |
| 5,936,035 | A | 8/1999 | Rhee et al. | 525/54.1 |
| 5,986,043 | A | 11/1999 | Hubbell et al. | 528/354 |
| 5,989,215 | A * | 11/1999 | Delmotte et al. | 604/82 |
| 6,017,301 | A | 1/2000 | Schwartz et al. | 547/781 |
| 6,051,248 | A | 4/2000 | Sawhney et al. | |
| 6,051,648 | A | 4/2000 | Rhee et al. | 525/54.1 |
| 6,063,061 | A | 5/2000 | Wallace et al. | 604/181 |
| 6,065,645 | A | 5/2000 | Sawhney et al. | |
| 6,065,654 | A | 5/2000 | Evensen | 223/113 |
| 6,124,273 | A | 9/2000 | Drohan et al. | 514/55 |
| 6,136,333 | A | 10/2000 | Cohn et al. | 424/423 |
| 6,162,241 | A | 12/2000 | Coury et al. | |
| 6,166,130 | A | 12/2000 | Rhee et al. | 525/54.1 |
| 6,201,065 | B1 | 3/2001 | Pathak et al. | |
| 6,238,403 | B1 | 5/2001 | Greene, Jr. et al. | 606/108 |
| 6,303,102 | B1 | 10/2001 | Schlichte | 424/10.3 |
| 6,312,725 | B1 | 11/2001 | Wallace et al. | 424/484 |
| 6,323,278 | B2 | 11/2001 | Rhee et al. | 525/54.1 |
| 6,348,558 | B1 * | 2/2002 | Harris et al. | 528/196 |
| 6,410,645 | B1 | 6/2002 | Pathak et al. | 525/78.02 |
| 6,458,889 | B1 | 10/2002 | Trollsas et al. | 525/54.1 |
| 6,465,001 | B1 | 10/2002 | Hubbell et al. | |

FOREIGN PATENT DOCUMENTS

| | | |
|---|---|---|
| EP | 246380 A3 | 11/1987 |
| EP | 0414848 B1 | 10/1995 |
| WO | WO 96/39212 | 12/1996 |
| WO | WO 97/19973 | 6/1997 |
| WO | WO 97/22371 | 6/1997 |
| WO | WO 97/22372 | 6/1997 |
| WO | WO 98/35631 | 8/1998 |
| WO | WO 99/08718 | 2/1999 |
| WO | WO 00/09087 | 2/2000 |
| WO | WO 015117 | 3/2000 |
| WO | WO 00/33764 | 6/2000 |
| WO | WO 01/68155 | 9/2001 |

OTHER PUBLICATIONS

Matrix VSG Vascular Sealing Gel Promational material.

Jacobs et al. "A Pressure-Balanced Sprayer for Intraaboinal Application of soluble Biomaterials in Laparoscopy," Abstract, presented in Chicago, Illinois, Mar. 2001.

Jacobs et al., "SprayGel™ as New Intraperitoneal Adhesion Prevention for Use in Laparoscopy and Laparotomy," Abstract, presented in Chicago, Illinois, Mar. 2001.

Ferland, et al., "Evaluation of SprayGel™ Adhesion Barrier System as a Barrier for the Prevention of Adhesion Formation After Gynecological Surgery," Abstract, presented in Chicago, Illinois, Mar. 2001.

Ferland et al., "Evaluation of a Sprayable Polyethyleen Glycol Adhesion Barrier in a Porcine Efficacy Model," Human Reproduction, vol. 16, No. 12, pp. 2718-2723, 2001.

Ferland et al., "Evaluatin of a Sprayable, Absorbable Adhesion Barrier in a new Porcine Adhesion Model," Abstract presented at the Global Congress of Gynecological Endoscopy, 29th Annual Meeting, American Association of Gynecological Laparoscopists, Nov. 15-19, 2000, Orlando, Florida.

Dunn et al., "Evaluation of the SprayGel™ Adhesion Barrier in the Rat Cecum Abrasion and Rabbit Uterine Horn Adhesion Models," Fertility and Sterility, vol. 75, No. 2, Feb. 2001, pp. 411-416.

Dunn et al., "Evaluation of Sprayable Postsurgical Adhesion Barrier in Two Rodent Models", Abstract presented at the Global Congress of Gynecological Endoscopy, 29th Annual Meeting, American Association of Gynecological Laparoscopists, Nov. 15-19, 2000, Orlando, Florida.

Audebert, "Initial Bordeaux Experience with Spraygel Adhesion Barrier System," Abstract presented at the 10th Congress of the European Society for Gynaecological Endoscopy, Nov. 21-24, Lisbon, PORTUGAL.

Mettler et al., "A Randomised Prospective Multi-Centre Clinical Trial of Spraygel as a Barrier for Prevention of Adhesion Formation After Gynaecological Surgery: An Interim Analysis", Abstract presented at the 10th Congress of the European Society for Gynaecological Endoscopy, Nov. 21-24, Lisbon, PORTUGAL.

US 6,214,374, 04/2001, Schmirler et al. (withdrawn)

* cited by examiner

| | |
|---|---|
| ⅠⅠⅠⅠ ─────── ⅠⅠⅠ | |
| FIG. 4P | |

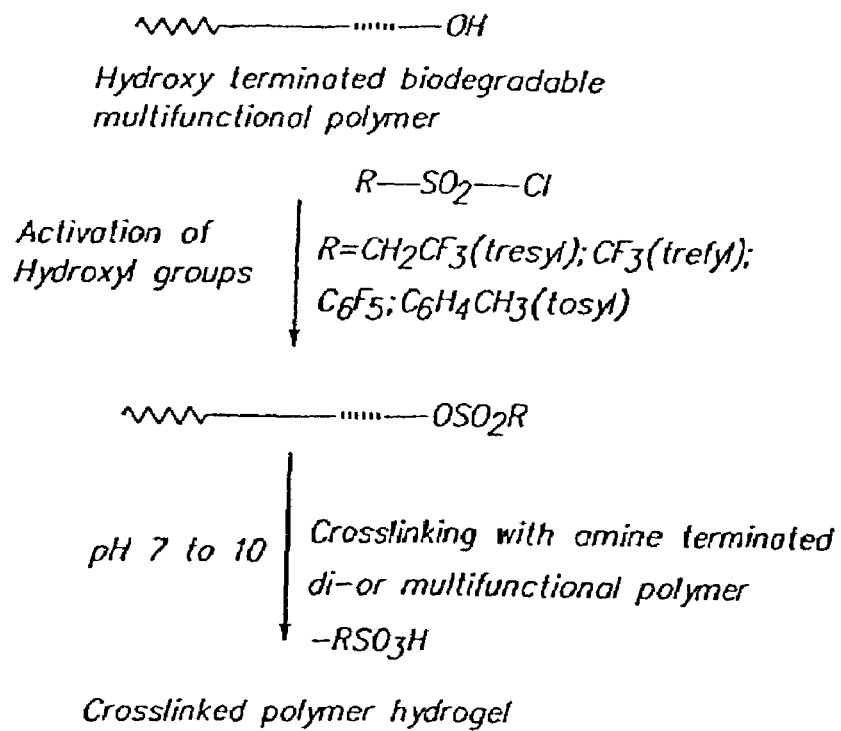
FIG. 7
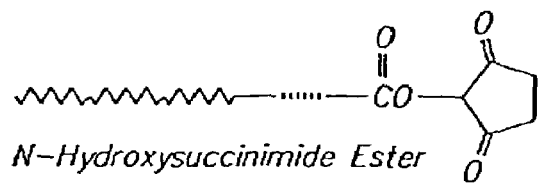
N-Hydroxysuccinimide Ester
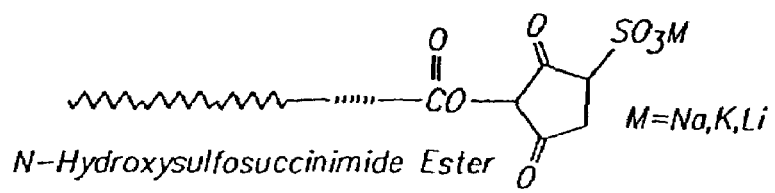
N-Hydroxysulfosuccinimide Ester
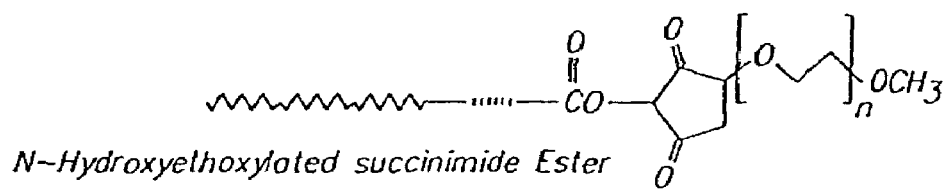
N-Hydroxyethoxylated succinimide Ester
FIG. 9

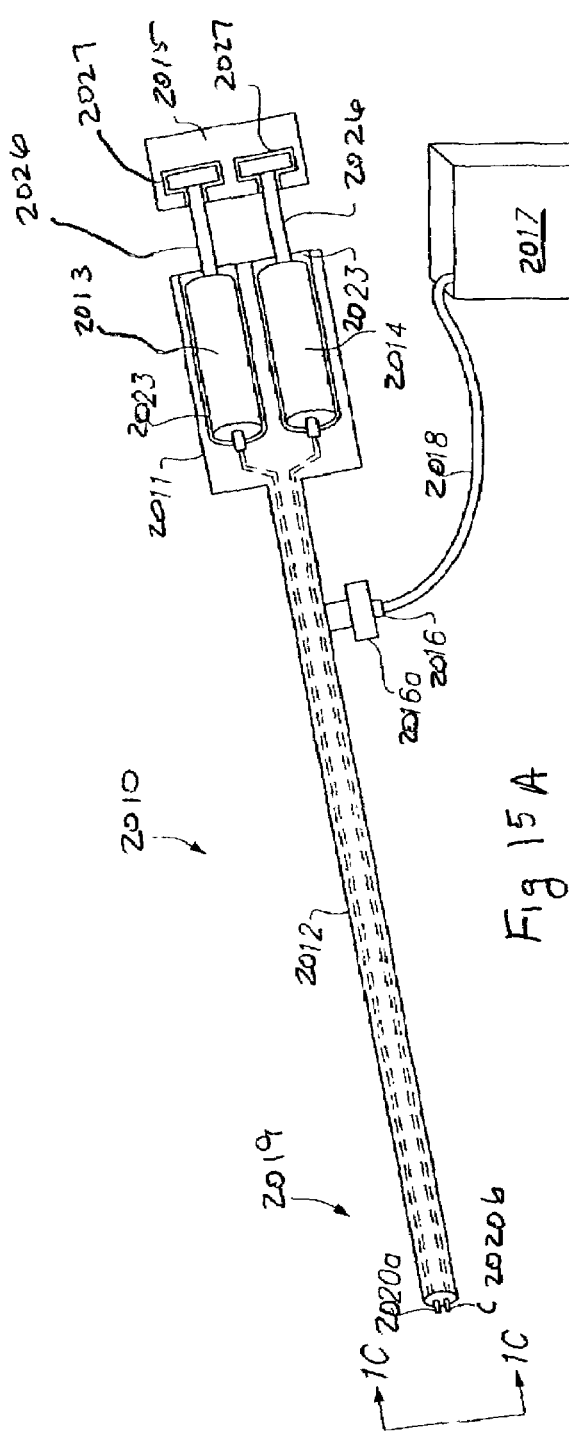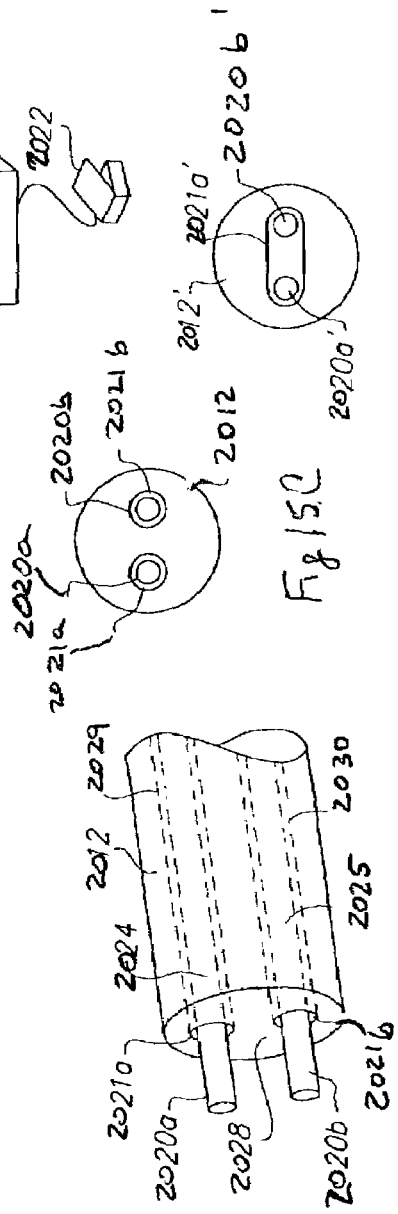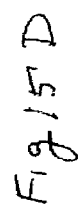

ADHESION BARRIERS APPLICABLE BY MINIMALLY INVASIVE SURGERY AND METHODS OF USE THEREOF

CROSS-REFERENCE TO RELATED APPLICATIONS

The present patent application is a Continuation-In-Part of U.S. patent application Ser. No. 10/010,715, filed Nov. 9, 2001 now U.S. Pat. No. 7,009,034, entitled "Biocompatible Crosslinked Polymers", which is a Continuation-In-Part of: U.S. patent application Ser. No. 09/454,900, filed Dec. 3, 1999, now U.S. Pat. No. 6,566,406 entitled "Biocompatible Crosslinked Polymers" which has a priority date based on U.S. Patent Application No. 60/110,849, filed Dec. 4, 1998. The present patent application also claims priority to U.S. Patent Application No. 60/359,236, filed Feb. 20, 2002, entitled "Sprayable Adhesions Barrier". All of these patents and patent applications are hereby claimed as priority documents and are hereby incorporated by reference herein.

FIELD OF THE INVENTION

The present invention relates generally to biocompatible crosslinked polymers, methods for preparing and using the same.

BACKGROUND OF THE INVENTION

Almost every surgical treatment carries a risk that bodily tissues exposed during the course of the surgery will adhere to each other, a condition termed an adhesion. Gynecological and abdominal surgeries, in particular, are prone to causing adhesions, which often have the appearance of scar-like masses. Adhesions are frequently painful and are a significant cause of infertility resulting from gynecological surgeries. Adhesions caused by surgeries are often called surgical adhesions.

One approach to the treatment of adhesions has been to coat surgically exposed tissues with a gel before closing the surgical site. Gels of various types have been used, including suspensions of colloidal particles, and pastes of natural polymers. Various examples of some of these approaches are described in U.S. Pat. Nos. 6,020,326 and 5,605,938. Some of these approaches allow for the polymers to be added to the patient "in situ" in a solution and then chemically reacted inside the patient so that the polymers form covalent crosslinks to create a polymer network. This approach lets the polymer be formed in a way that closely conforms to the shape of the tissues in the body, as described, for example, in U.S. Pat. Nos. 5,410,016; 5,573,934 and 5,626,863.

Hydrogels are especially useful for use in the body because they are more biocompatible than non-hydrogels and are thus better tolerated in the body. Besides being useful for post-operative adhesions they can be used for many medical purposes, such as tissue augmentation, medical device coating, surgical sealing, and drug delivery. Examples of hydrogels formulated for such purposes are found in U.S. Pat. Nos. 4,414,976; 4,427,651; 4,925,677; 5,527,856; 5,550,188; and 5,814,621.

Crosslinked polymers have previously been formed using polymers equipped with either electrophilic or nucleophilic functional groups. For example, U.S. Pat. Nos. 5,296,518 and 5,104,909 to Grasel et al. describe the formation of crosslinked polymers from ethylene oxide rich prepolymers, wherein a polyisocyanate or low molecular weight diisocyanate is used as the electrophilic polymer or crosslinker, and a polyoxyethylene based polyol with in situ generated amine groups is used as the nucleophilic precursor; see also U.S. Pat. Nos. 5,514,379; 5,527,856; and 5,550,188.

SUMMARY OF THE INVENTION

An embodiment of the invention is a system for coating a tissue, with the system including a first synthetic reactive precursor species, a second synthetic reactive precursor species, and a minimally invasive surgical applicator for delivering the first and the second reactive precursor species. In certain embodiments, upon delivery, the first reactive precursor species and the second reactive precursor species interact with each other to spontaneously form a biocompatible, covalently crosslinked hydrogel coating on the tissue.

An embodiment of the invention is a system for coating a tissue of a patient with a hydrogel. The embodiment of the system has a minimally invasive surgical applicator having a first nozzle coupled to a first conduit in fluid communication with a first chamber, and a second nozzle coupled to a second conduit in fluid communication with a second chamber, with the first chamber holding a first reactive precursor species and the second chamber holding a second reactive precursor species; wherein the first and second nozzles cooperate with a source of pressurized gas and mixes the first reactive precursor species with the second reactive precursor species to spontaneously form a biocompatible, covalently crosslinked hydrogel coating on the tissue.

An embodiment of the invention is a method of coating a patient's tissue by using minimally invasive surgical techniques to deliver a first and a second reactive synthetic reactive precursor species and to mix the reactive precursor species in situ to interact with each other to spontaneously form a biocompatible, covalently crosslinked, hydrogel coating adherent to the tissue. In certain embodiments, a synthetic or natural hydrogel is suitable.

An embodiment of the invention is a hydrogel for use on a substrate such as a patient's tissue. The hydrogel has water, an optional biocompatible visualization agent, and reactive hydrophilic polymers that form a crosslinked hydrogel after contact with the tissue. The hydrogel coats the tissue and forms a coating. The coating may have a free surface. The visualization agent is disposed in the hydrogel and reflects or emits light at a wavelength detectable to a human eye. This feature lets a user applying the hydrogel observe the hydrogel and estimate its thickness and apply the hydrogel until it reaches a predetermined thickness.

The hydrophilic polymers may be natural polymers, for example proteins e.g., collagen, fibrinogen, albumin, and fibrin, polysaccharides, or glycosaminoglycans. The polymers can also have a hydrolytically biodegradable portion and/or a proteolytically degradable portion. The polymers are preferably covalently crosslinked and are crosslinkable via an electrophilic functional group-nucleophilic functional group reaction. An embodiment of the invention is a hydrogel that is coated onto a tissue and has a maximum thickness of between 0.1 to 10.0 mm.

Preferred biocompatible visualization agents are FD&C Blue #1, FD&C #2 (indigo carmine), FD&C Green #6, and methylene blue. The visualization agent may also be a fluorescent molecule. The visualization agent is preferably not covalently linked to the hydrogel.

Methods for using the polymeric compositions to coat a tissue include mixing hydrophilic precursor polymers with chemically distinct reactive functional groups such that they form crosslinks via nucleophilic-electrophilic reaction after mixing and contact with the tissue. The polymers crosslink to form a biodegradable hydrogel. A preferred application is to prevent surgical adhesions by applying the hydrogel as a coating on a tissue substrate and maintaining another surface of the hydrogel as a free surface. A visualization agent is preferably included so that the visualization agent is disposed within the hydrogel and reflects or emits light at a wavelength detectable to a human eye. A preferred method of use is to form a hydrogel on the tissue until the color and/or color intensity of the hydrogel indicates that a predetermined thickness of hydrogel has been deposited on the tissue.

An embodiment of the invention is a polymeric product made by a process of mixing hydrophilic polymers having nucleophilic functional groups with hydrophilic polymers having electrophilic functional groups such that they form a mix that crosslinks after contact with the tissue of a patient to form a biodegradable hydrogel that coats a tissue. In many applications it is desirable to also have a free surface. The hydrogel preferably contains a visualization agent in the mix of reactive precursor species so that the visualization agent is disposed within the interior and reflects or emits light at a wavelength detectable to a human eye.

An embodiment of the invention is a kit having a biocompatible visualization agent, at least two chemically distinct reactive precursor species, and instructions for using the visualization agent and the reactive precursor species such that the reactive precursor species may be combined to form crosslinked hydrophilic polymers that form a biodegradable hydrogel. In another embodiment, the visualization agent is premixed with one of the reactive precursor species.

It is an embodiment of the present invention to provide biocompatible crosslinked polymers and methods for their preparation and use, in which the biocompatible crosslinked polymers are formed without using free radical chemistry, and are formed using at least one non-toxic small molecule precursor.

It is an embodiment of this invention to provide such biocompatible crosslinked polymers and methods for their preparation and use, in which the biocompatible crosslinked polymers are formed from aqueous solutions, preferably under physiological conditions.

It is an embodiment of this invention to provide such biocompatible crosslinked polymers and methods for their preparation and use, in which the biocompatible crosslinked polymers are formed in vivo.

It is an embodiment of this invention to provide such biocompatible crosslinked polymers and methods for their preparation and use, in which the biocompatible crosslinked polymers are biodegradable.

It is an embodiment of this invention to provide such biocompatible crosslinked polymers and methods for their preparation and use, in which the biocompatible crosslinked polymers, their precursors, or both are colored.

It is an embodiment of this invention to provide methods for preparing tissue conforming, biocompatible crosslinked polymers in a desirable form, size and shape.

It is an embodiment of this invention to provide methods for using biocompatible crosslinked polymers to form medically useful devices or implants for use as surgical adhesion prevention barriers, as implantable wound dressings, as scaffolds for cellular growth for tissue engineering or as surgical tissue adhesives or sealants.

It is an embodiment of this invention to provide methods for using biocompatible crosslinked polymers to form medically useful devices or implants that can release bioactive compounds in a controlled manner for local, systemic, or targeted drug delivery.

An embodiment of this invention provides methods and compositions for producing composite biomaterials comprising fibers or particulates made of biodegradable biocompatible crosslinked polymers.

BRIEF DESCRIPTION OF THE DRAWINGS

FIG. 7 depicts the use of sulfonyl chloride activation chemistry to prepare an electrophilic functional polymer.

FIG. 9 depicts preferred NHS esters for use in the invention.

FIGS. 15A, 15B, and 15C, are, respectively, a perspective view of a two-fluid sprayer of the present invention, a detailed view of the distal end of the sprayer, and an end view of the distal end of the sprayer taken along line 1C-1C of FIG. 20A.

FIG. 15D is an end view of the distal end of an alternative embodiment of the sprayer of FIG. 19A taken along line 1C-1C.

DETAILED DESCRIPTION OF THE INVENTION

Figure 1A:
FIG. 1 depicts electrophilic functional group water soluble and biodegradable crosslinkers or functional polymers, which can be crosslinked with appropriate nucleophilic functional group precursors.
Figure 1B:
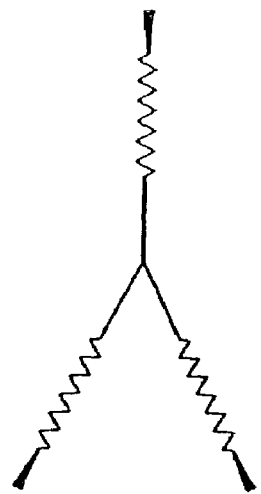
Figure 1C:
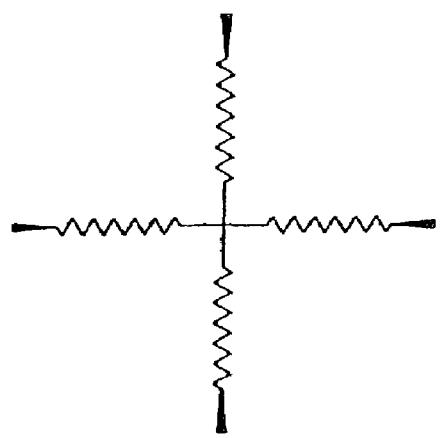
Figure 1E:
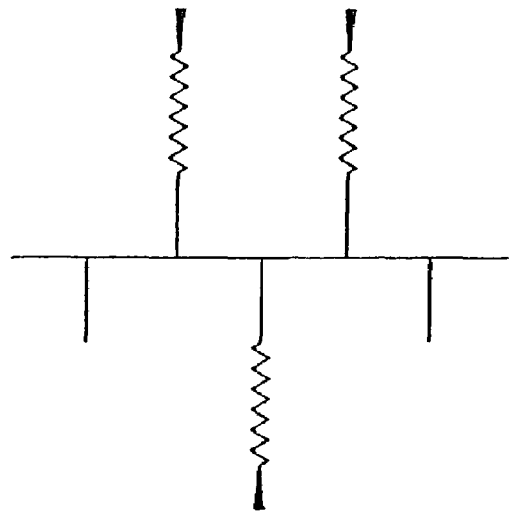
Figure 1D:
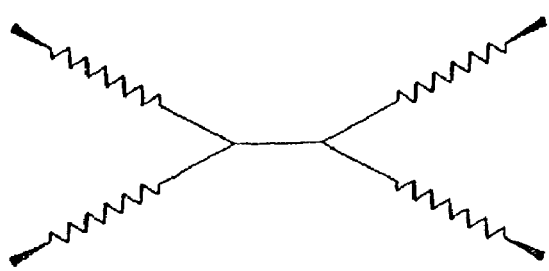
Figure 2F:
FIG. 2 depicts nucleophilic water soluble and biodegradable crosslinkers or functional polymers, which can be crosslinked with appropriate electrophilic precursors.
Figure 2G:
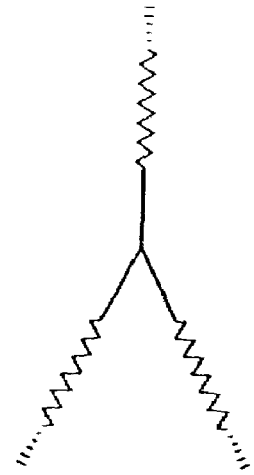
Figure 2H:
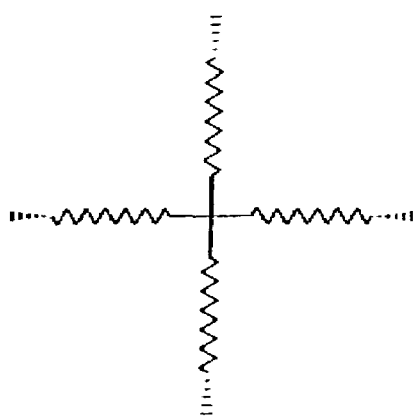
Figure 2J:
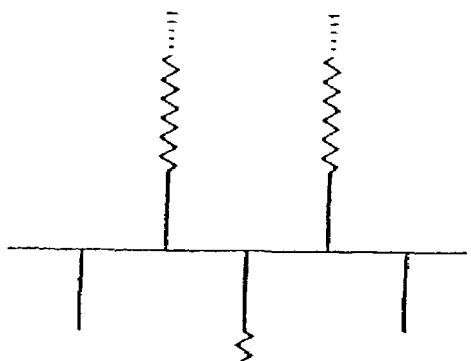
Figure 2I:
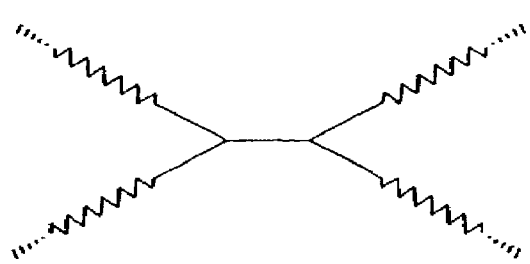
Figure 3K:
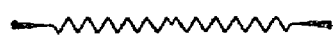
FIG. 3 depicts electrophilic water soluble and biodegradable crosslinkers or functional polymers, which can be crosslinked with appropriate nucleophilic functional group precursors, wherein either the biodegradable linkages or the functional groups are selected so as to make the precursor water soluble.
Figure 3L:
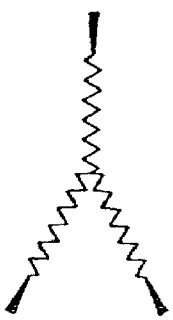
Figure 3M:
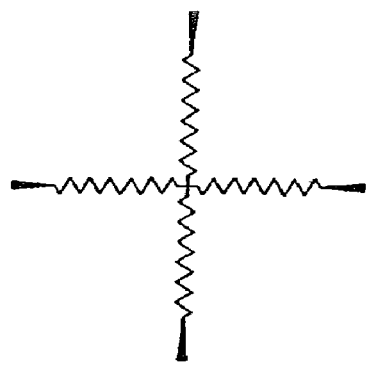
Figure 3O:
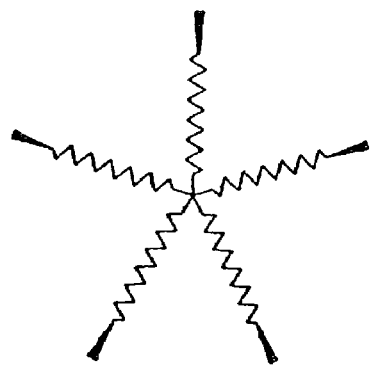
Figure 3N:
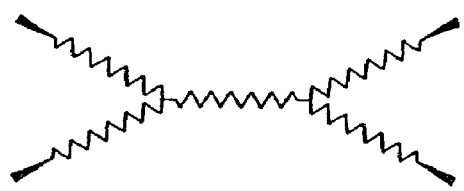
Figure 4Q:
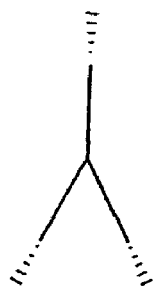
FIG. 4 depicts nucleophilic functional group water soluble crosslinkers or functional polymers, which can be crosslinked with appropriate electrophilic functional group precursors, and which are not biodegradable.
Figure 4T:
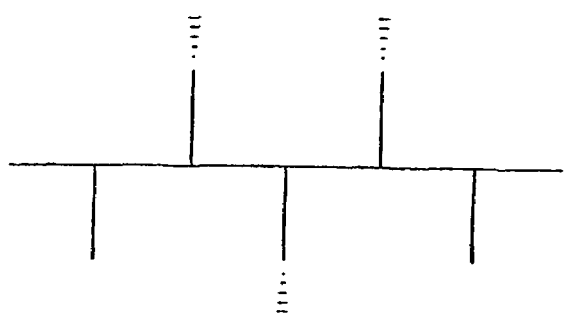
Figure 4R:
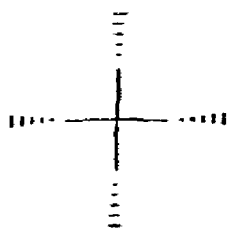
Figure 4S:
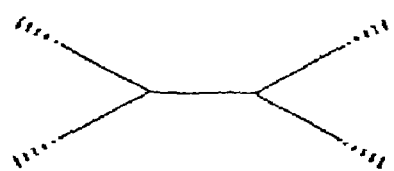
Figure 5U:
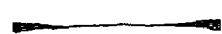
FIG. 5 depicts electrophilic water soluble crosslinkers or functional polymers, which can be crosslinked with appropriate nucleophilic functional group precursors, and which are not biodegradable.
Figure 5V:
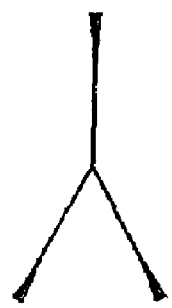
Figure 5W:
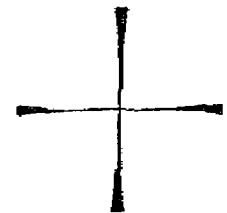
Figure 5Y:
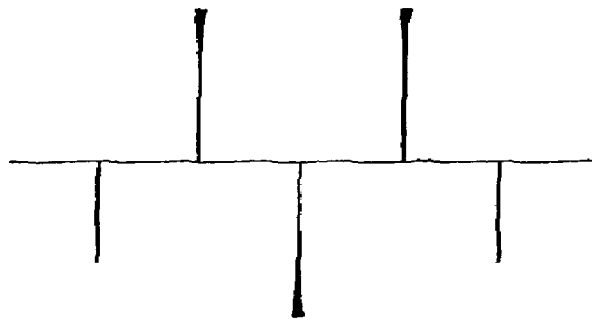
Figure 5X:
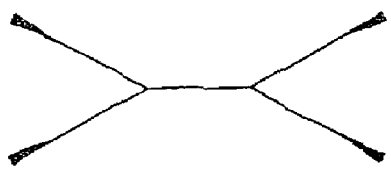

The invention has embodiments for using minimally invasive surgical (MIS) procedures to form hydrogels on tissues by combining components on the tissues that form the hydrogel. The components may include, for example, reactive precursors having nucleophilic or electrophilic functional groups, or a precursor polymerizable by free radical mechanisms. In some embodiments, MIS applicators for applying the components are adapted to spray the components onto the target tissue. In some embodiments, the components do not require the application of external energy, e.g., light, to form a hydrogel.

MIS presents challenges that are not present in conventional open surgery. For example, MIS instruments are difficult to use compared to conventional surgical tools because the user must work through an opening that is of a limited size. As a result, MIS instruments are difficult to maneuver and orient relative to instruments that are used during open surgeries.

Also, MIS usually involves introducing gas into the patient's tissue to expand the area that the surgeon may work in. MIS procedures typically involve using instruments that deliver gas to the patient so that the instruments and procedures are relatively complicated compared to open surgery tools.

The use of the gas complicates the performance of products that undergo chemical reactions in situ in the patient during MIS. The gas is conventioanlly $CO_2$, which can cause the failure of many chemical reactions that are successful in open surgery applications. Open surgery applications are performed under essentially atmospheric conditions, so a $CO_2$ environment is a different environment than an open surgery environment. Free radical polymerization chemistries may typically be accomplished in a $CO_2$ environment, but electrophile-nucleophile reactions are slowed in a $CO_2$ atmosphere. A slow reaction can cause a hydrogelation procedure to fail because solutions of hydrogel precursors flow off of tissues before they react to form the hydrogel, physical properties of the hydrogel may be changed, a slow reaction may be less complete, and the precursors may become involved in too many unwanted side reactions, e.g., hydrolysis of the functional groups.

One technique for performing electrophile-nucleophile reactions is to introduce air into the patient, as described in U.S. Pat. No. 6,179,862. A concentration of more than about 25% air in the introduced gas is believed to be preferable.

The introduction of gas, however, can result in a pressure build-up in the patient's body unless a mechanism is provided for venting the excess gas, as described, for example, in U.S. Pat. No. 6,179,862.

Further, the formation of hydrogels in situ on a tissue using MIS is difficult compared to open surgery because gravity and the geometry of the tissue become relatively more important. Hydrogel precursors may be poured into the opening in a patient during open surgery and allowed to flow into the patient until the fluids cover all of the desired tissue areas. Or the precursors may be poured in while the user manipulates the target tissues to a conformation that holds the precursors until they gel. The hydrogel thus eventually covers the target tissue because gravity allows delivery of the precursors downwards to the patient and holds the hydrogel in place over the target tissue until it attains sufficient mechanical strength and/or adherence to remain in that position. During MIS, however, the applicator for applying hydrogel precursors is often not oriented above the target tissue. Gravity tends to force the precursors off of the tissues. As an example, an ovary has a convex surface, with the result that fluids applied to an ovary typically flow off the ovary under the influence of gravity. Further, in an MIS application, the applicator is not typically positioned on top of the ovary. Therefore compositions that are suitable in an open surgery are often not suitable for use on the ovary. For these reasons, formulations and techniques for making gels in situ that are suitable for use in an open surgery application are often not useful for MIS applications.

Furthermore, the present inventors have realized that use of color in biocompatible crosslinked polymers and/or reactive precursor species improves the performance of crosslinked networks of polymers and/or reactive precursor species in a surgical environment, especially for minimally invasive surgical procedures. Many applications have the best results when an appropriate or predetermined amount of hydrogel is delivered to the surgical environment, for example when applied to the surface of a substrate such as a tissue. A hydrogel that is too thick may reduce efficiency or interfere with other surgical aspects. For example, if a hydrogel is applied too thickly, it could interfere with closure of the wound or interfere with tissue movement, e.g., in intestinal applications. A hydrogel that is too thin will not serve its purpose, e.g., providing a barrier that prevents surgical adhesions or provides a strong seal against fluid leakage. The introduction of a visualization agent allows the user to determine the thickness of the applied hydrogel. The visualization agent is preferably an agent that provides a color that is visible to the human eye, e.g., a color that is detected visually by the user or detected by a video camera and relayed to a video screen observed by the user.

Conventional polymeric hydrogels may sometimes have a faint inherent color or develop a faint color as a result of chemical activity, but their lack of color makes a layer of a hydrogel very difficult to see after it has been applied to a tissue. Hydrogels have sometimes been mixed with image contrast agents to increase their visibility for medical imaging devices such as X-ray or magnetic resonance imaging (MRI) machines, as in, for example, U.S. Pat. No. 5,514, 379. Colorants have also been used for hydrogels injected into bodily tissues, for example in U.S. Pat. Nos. 5,514,379 and 6,124,273.

The use of a visualization agent is especially preferred when a hydrogel is used to coat a substrate. A substrate coating surface is a surface of a hydrogel that contacts a substrate and, in the region of contact, is essentially in continuous contact with that substrate. Although some small portions of the coating or substrate may not be in contact, the contact is intimate. A substrate coating surface can be formed when the hydrogel crosslinks after contacting the substrate surface because the contact before crosslinking allows the hydrogel precursors to mix and conform to the shape of the substrate. A preformed hydrogel material generally does not have a substrate coating surface and may be able to move relative to the substrate. A preferred substrate is a tissue of a patient.

A hydrogel with a substrate coating surface preferably also has a free surface when the hydrogel is used for prevention of adhesions. The hydrogel is applied to a tissue and crosslinks while having one free surface that is not adherent to any tissue but is instead freely movable relative to any tissues that it may subsequently contact. The free surface prevents the coated tissue from contact with other tissues and does not prevent the movement of other tissues so that protection and free movement are optimal. In this situation, a user that applies the hydrogel may observe the hydrogel by looking through the free surface into the hydrogel and at the coated tissue. A visualization agent in the hydrogel makes the hydrogel change in its appearance until the user determines that the thickness of the hydrogel is sufficient. For example, a blue dye in the hydrogel makes the hydrogel increasingly opaque as the thickness of the hydrogel increases.

It is preferable to provide color by adding a colored visualization agent to the hydrogel precursors before crosslinking. The coloring agent is thus present in a premixed amount that is already selected for the application. A preferred embodiment of the invention uses biocompatible crosslinked polymers formed from the reaction of precursors having electrophilic functional group and nucleophilic functional groups. The precursors are preferably water soluble, non-toxic and biologically acceptable.

Preferably, at least one of the precursors is a small molecule of about 1000 Da or less, and is referred to as a "crosslinker" because it can crosslink other precursors, e.g., macromers and polymers. The crosslinker preferably has a solubility of at least 1 g/100 mL in an aqueous solution. A crosslinked molecule may be crosslinked via an ionic or covalent bond, a physical force, or other attraction. Preferably, at least one of the other precursors is a macromolecule, and is referred to as a "functional polymer". The macromolecule, when reacted in combination with a small molecular weight crosslinker, is preferably at least five to fifty times greater in molecular weight than the small molecular weight crosslinker and is preferably less than about 60,000 Da. A more preferred range is a macromolecule that is seven to thirty times greater in molecular weight than the crosslinker and a most preferred range is about ten to twenty times difference in weight. Further, a macromolecular molecular weight of 5,000 to 50,000 is preferred, a molecular weight of 7,000 to 40,000 is more preferred and a molecular weight of 10,000 to 20,000 is most preferred. Alternatively, if a macromolecule is used to crosslink, then the functional polymer and the macromolecule may be of relatively similar molecular weights, with preferred ranges of molecular weights as described above. The term polymer, as used herein, means a molecule formed of at least three repeating groups. The term "reactive precursor species" means a polymer, functional polymer, macromolecule, small molecule, or crosslinker that can take part in a reaction to form a network of crosslinked molecules, e.g., a hydrogel.

An embodiment of the invention is a hydrogel for use on a patient's tissue that has water, a biocompatible visualization agent, and crosslinked hydrophilic polymers that form a hydrogel after contact with the tissue. The hydrogel coats the tissue and also has a free surface. The visualization agent reflects or emits light at a wavelength detectable to a human eye so that a user applying the hydrogel can observe the gel and also estimate its thickness.

Natural polymers, for example proteins or glycosaminoglycans, e.g., collagen, fibrinogen, albumin, and fibrin, may be crosslinked using reactive precursor species with electrophilic functional groups. Natural polymers are proteolytically degraded by proteases present in the body. Synthetic polymers and reactive precursor species are preferred, however, and may have electrophilic functional groups that are carbodiimidazole, sulfonyl chloride, chlorocarbonates, n-hydroxysuccinimidyl ester, succinimidyl ester or sulfasuccinimidyl esters. Groups such as isocyanates or thiocyanates are less preferable since they tend to produce potentially toxic byproducts. The term synthetic means a molecule that is not found in nature, e.g., polyethylene glycol. The nucleophilic functional groups may be, for example, amine, hydroxyl, carboxyl, and thiol. The polymers preferably have a polyalkylene glycol portion. More preferably they are polyethylene glycol based. The polymers preferably also have a hydrolytically biodegradable portion or linkage, for example an ester, carbonate, or an amide linkage. Several such linkages are well known in the art and originate from alpha-hydroxy acids, their cyclic dimmers, or other chemical species used to synthesize biodegradable articles, such as, glycolide, dl-lactide, l-lactide, caprolactone, dioxanone, trimethylene carbonate or a copolymer thereof. Other linkages such as carboxymethyl hydroxybutyrate or propinoic acid hydroxybutarate are also suitable, see PCT Application No. WO 99/14259, "Degradable Poly (Ethylene Glycol) Hydrogels with Controlled Half-Life and Precursors Therefore", which is hereby incorporated by reference herein. A preferred embodiment has reactive precursor species with two to ten nucleophilic functional groups each and reactive precursor species with two to ten electrophilic functional groups each. The hydrophilic species are preferably synthetic molecules.

Preferred biocompatible visualization agents are FD&C blue #1, FD&C blue #2 (indigo carmine), and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. These concentration ranges were found to give a color to the hydrogel that was desirable without interfering with crosslinking times (as measured by the time for the reactive precursor species to gel). The visualization agent may also be a fluorescent molecule. The visualization agent is preferably not covalently linked to the hydrogel. The visualization agent, however, may be crosslinked to the hydrogel at the time of polymerization or by using a precursor having visualization agent already crosslinked thereto.

An embodiment of the invention is a hydrogel that is coated onto a tissue and generally has at least a portion with a thickness of between 0.8 to 12.0 mm. One technique for measuring the thickness is to create a hydrogel on a test surface and use a micrometer to measure thicknesses at various points. Alternatively, a calibrated videomicroscopic image could be used. The preferred thickness depends on the medical application but a preferred thickness for prevention of surgical adhesions is about 0.5 to 10.0 mm, and more preferably about 0.8 to 5 mm and even more preferably about 1-3 mm.

A preferred method of use is to form a hydrogel on the tissue until the color of the hydrogel indicates that a predetermined thickness of hydrogel has been deposited on the tissue. The deposition of the precursors that result in formation of the hydrogel may be by spraying, dripping, or delivery via a catheter. The user may apply the hydrogel to a test surface with a color that resembles the surface that the user contemplates using and observe the color that results when the hydrogel reaches a desired thickness that the user has predetermined. In use, the user applies the hydrogel until the desired color is reached. A typical patient's tissue has a pinkish appearance and the microvasculature can be observed as thin lines. One embodiment is to introduce a concentration of visualization agent into the hydrogel so that the user applies the hydrogel until the microvasculature is no longer visible through the hydrogel, at which point the hydrogel is a desired thickness. Another suitable method is to apply the hydrogel until the underlying tissue is obscured. An appropriately selected concentration of visualization agent is used so that the hydrogel obscures the tissue features when the hydrogel achieves a predetermined thickness. The predetermined thickness is chosen to correspond to the particular application. In these thickness evaluation approaches, a concentration that is too low will result in a hydrogel that is too thick and a concentration that is too high will result in a hydrogel that is too thin. Thus, the visualization agent allows the user to ascertain the presence of the hydrogel on the surface and also gain feedback on the appropriate thickness, preferably in combination with instructions provided as part of a kit. In some embodiments, suitable approaches can be used with visualization agents and polymers that crosslink by, for example, free radical polymerization, electrophilic functional group-nucleophilic functional group interaction. An advantage of electrophilic-nucleophilic polymerization mechanisms compared to free radical polymerization mechanisms is that free radicals would tend to bleach the visualization agents and thereby interfere with visualization of the hydrogel. Thus visualization agents chosen for use with free radical systems are preferably chosen to reduce bleaching.

An embodiment of the invention is a method of a user applying a hydrogel coating to a substrate and selecting a visually observable visualization agent to observe the hydrogel coating. The user may use visualization agents to see the hydrogel with the human eye or with the aid of an imaging device that detects visually observable visualization agents, e.g., a videocamera. A visually observable visualization agent is an agent that has a color detectable by a human eye. A characteristic of providing imaging to an X-ray or MRI machine is not a characteristic sufficient to establish function as a visually observable visualization agent. An alternative embodiment is a visualization agent that may not normally be seem by the human eye but is detectable at a different wavelength, e.g., the infra red or ultraviolet, when used in combination with a suitable imaging device, e.g., a videocamera.

A coating has a surface that can be viewed for use with a visually observable visualization agent. In contrast, a hydrogel injected into a blood vessel, muscle, or other tissue has essentially no surface for viewing a visualization agent because its surface area is essentially engaged with tissues of the patient. Further, polymers injected into a tissue lack a surface that is disposed on the surface of a tissue and do not provide a means for a user to control the thickness of the coating on the surface of the tissue. Hydrogels that are merely injected into a patient's body would not be equivalent to embodiments of the present invention that involve a hydrogel coating on a substrate and are inoperative for embodiments of the invention that entail use of a visualization agent in a hydrogel coating.

An embodiment of the invention involves a mixture or a process of mixing hydrophilic reactive precursor species having nucleophilic functional groups with hydrophilic reactive precursor species having electrophilic functional groups such that they form a mixture that crosslinks quickly after contact with the tissue of a patient to form a biodegradable hydrogel that coats and adheres to a tissue. This may be achieved by making reactive precursor species that crosslink quickly after mixing. Hydrophilic reactive precursor species can be dissolved in buffered water such that they provide low viscosity solutions that readily mix and flow when contacting the tissue. As they flow across the tissue, they conform to the shape of the small features of the tissue such as bumps, crevices and any deviation from molecular smoothness. If the reactive precursor species are too slow to crosslink, they will flow off the tissue and away into other portions of the body with the result that the user will be unable to localize the hydrogel on the desired tissue. Without limiting the invention to a particular theory of operation, it is believed that reactive precursor species that crosslink appropriately quickly after contacting a tissue surface will form a three dimensional structure that is mechanically interlocked with the coated tissue. This interlocking contributes to adherence, intimate contact, and essentially continuous coverage of the coated region of the tissue.

Adherence is important for medical applications that require a coating, e.g., for prevention of adhesions, since a user must be able to place the hydrogel in the portions of the patient that are needful, for example, around an ovary or surrounding an intestine. Further, the hydrogel must remain on the intended tissue or it will be unable to provide a prophylactic barrier. The hydrogels of the invention have good adhesion onto tissue and are useful for all applications wherein surgical glues have previously been used. For example, sealing of the dura mater of the brain to prevent leakage of cerebrospinal fluid may be accomplished with combinations of reactive precursor species described herein by using reactive precursor species with nucleophilic functional groups for mixing with hydrophilic reactive precursor species having electrophilic functional groups to form a mix that crosslinks quickly after contact with the tissue of a patient, e.g., the dura mater, to form a hydrogel that coats a tissue.

A simple dip test that shows that a hydrogel has adherence. To perform this test, a gel of about 5×5 centimeters in length×width and about 4 to 10 mm in thickness is formed on a substrate, the hydrogel is immersed in water or physiological saline for five minutes, removed, and tilted to an angle of 90 degrees above horizontal, and dipped into and out of a vessel of physiological saline five times at a rate of about 10 mm per second so that the hydrogel passes through the air-water interface ten times. Then the substrate is rotated about 90 degrees so that the substrate is approximately horizontal and the hydrogel is below the substrate. The substrate is left in this position for five minutes. The gel passes the dip test if less than about 1 square centimeter of the gel is then observed to be separated from the substrate. If the substrate lacks stiffness, it may be affixed to a stiff support so that it may tested. Physiological saline, in the context of the dip test, means a saline solution with an approximately physiological osmolarity and a pH of 7.0-7.4 at room temperature that is customarily used in cell culture, for example, phosphate buffered saline. As used herein, the gel has adherence to a substrate if it passes the dip test.

Suitable crosslinking times vary for different applications. In most applications, the crosslinking reaction leading to gelation occurs within about 10 minutes, more preferably within about 2 minutes, even more preferably within 10 seconds. In the case of most surgical adhesion prevention and tissue sealing applications, it is preferable to use a hydrogel that crosslinks in less than about 10 seconds and more preferably in about 2-4 seconds in order to allow a user to make multiple passes with a hydrogel applicator tool such as a sprayer; see, for example commonly assigned U.S. Pat. Nos. 6,179,862; 6,165,201; 6,152,943; and U.S. patent application Ser. No. 09/687,588, which are hereby incorporated herein by reference. In the case of tissues that can be accessed only indirectly, longer times are most preferable to allow the gel a longer time to flow into the inaccessible space. For example, application of an adhesion barrier in and around the spinal cord and exiting nerve roots following spine surgery may require several extra seconds to penetrate around the complex geometry of the tissues so that a preferred time is between about 5 and about 90 seconds and more preferably between about 10 and about 30 seconds. The Examples herein describe a variety of reactive precursor species and methods of making reactive precursor species that may be mixed to provide crosslinked networks that crosslink quickly after mixing such that one skilled in these arts will understand how to make the materials of the invention after reading this disclosure.

MIS Applicators and Applications

Certain embodiments of the invention may be used in an MIS, for example, devices and methods as set forth in U.S. Pat. No. 6,179,862, which describes a MIS sprayer for applying two or more crosslinkable components to tissue to form a coating in situ, describes using a vent for venting gas from the patient, and describes introducing air into the patient. For example, two crosslinkable precursor solutions, each containing one component of a co-initiating system capable of crosslinking when mixed together, may be placed in separate chambers of the sprayer. When the sprayer is activated, the emergent spray contacts tissue, resulting in mixing and crosslinking of the two solutions to form a coating (for example a hydrogel) on the tissue surface.

In a preferred embodiment, the sprayer comprises separate spray nozzles for each of two or more crosslinkable solutions, with each nozzle surrounded by a separate or common gas flow outlet. The crosslinkable solutions are stored in separate compartments, e.g., a multi-cylinder syringe, and communicated under pressure to the spray nozzles. In the presence of gas flow through the gas flow outlets, the crosslinkable solutions are atomized and mixed in the gas flow to form a spray, which may be used to coat tissue.

In certain embodiments, a $CO_2$ gas cartridge is reversibly or permanently mounted on the device to facilitate delivery of the precursors.

The crosslinkable solutions used with the apparatus may be crosslinked using either physical crosslinking, chemical crosslinking, or both. For a chemical initiation process, the two or more crosslinkable solutions may polymerize when mixed in the gas flows during spraying, thus forming an adherent coating that adheres to the tissue surface on contact. If a thermal initiating process is used, the two or more solutions may crosslink after contacting the tissue surface and warming to physiological temperatures.

Alternatively, the two or more solutions may include macromers that contain groups that demonstrate activity towards other functional groups such as amines, imines, thiols, carboxyls, isocyanates, urethanes, amides, thiocyanates, hydroxyls, etc., which may be naturally present in, on, or around tissue or may be optionally provided in the region as part of the instilled formulation required to effect the barrier.

The present invention includes embodiments directed to the use of multi-component crosslinkable solutions to form protective coatings on tissue, e.g., to prevent post-surgical adhesions, or as drug delivery layers. In accordance with the methods of certain embodiments of the present invention, two or more crosslinkable precursor solutions are sprayed onto tissue during, or near the completion, of surgery to form adherent coatings. The following written description describes certain multi-component hydrogel systems suitable for such use, apparatus for dispensing such hydrogel systems, and provides illustrative examples of use of certain of the inventive methods and apparatus.

Crosslinkable solutions preferred for use in accordance with the principles of the present invention include those that may be used to form coatings on tissue, and may form physical crosslinks, chemical crosslinks, or both. Physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc. Chemical crosslinking may be accomplished by any of a number of mechanisms, including free radical polymerization, condensation polymerization, anionic or cationic polymerization, step growth polymerization, and the like.

Hydrogels suitable for use in accordance with the principles of the present invention preferably crosslink spontaneously without requiring the use of a separate energy source. Such systems allow good control of the crosslinking process, because gelation does not occur until the sprayer is actuated and mixing of the two solutions takes place. If desired, one or both crosslinkable solutions may contain dyes or other means for visualizing the hydrogel coating. Alternatively, a colored compound may be produced as a byproduct of the reactive process. The crosslinkable solutions also may contain a bioactive drug or therapeutic compound that is entrapped in the resulting coating, so that the coating becomes a drug delivery layer.

Water soluble polymerizable polymeric monomers having a functionality >1 (i.e., that form crosslinked networks on polymerization) and that form hydrogels are referred to hereinafter as "macromers". Several functional groups may be used to facilitate chemical crosslinking reactions. When these functional groups are self condensable, such as ethylenically unsaturated functional groups, the crosslinker alone is sufficient to result in the formation of a hydrogel, when polymerization is initiated with appropriate agents. Where two solutions are employed, each solution preferably contains one component of a co-initiating system and crosslink on contact. The solutions are stored in separate compartments of a sprayer, and mixed either when sprayed or on contact with the tissue.

An example of an initiating system suitable for use in the present invention is the combination of a peroxygen compound in one solution, and a reactive ion, such as a transition metal, in another. Other means for polymerization of macromers to coatings on tissue also may be advantageously used with macromers that contain groups that demonstrate activity towards functional groups such as amines, imines, thiols, carboxyls, isocyanates, urethanes, amides, thiocyanates, hydroxyls, etc., which may be naturally present in, on, or around tissue. Alternatively, such functional groups optionally may be provided in the region as part of the instilled formulation required to effect the barrier. In this case, no external initiators of polymerization are needed and polymerization proceeds spontaneously when two complementary reactive functional groups containing moieties interact at the application site.

Preferred hydrogel systems are those biocompatible multi-component systems that spontaneously crosslink when the components are mixed, but wherein the two or more components are individually stable for the duration of the deposition process. Such systems include, for example, contain macromers that are di or multifunctional amines in one component and di or multifunctional oxirane containing moieties in the other component. Other initiator systems, such as components of redox type initiators, also may be used. The mixing of the two or more solutions may result in either an addition or condensation polymerization that further leads to the formation of a coating.

Any monomer capable of being crosslinked to form a biocompatible surface coating may be used. The monomers may be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, U.S. Pat. Nos. 4,741,872 and 5,160,745 to De Luca et al., or U.S. Pat. No. 5,410,016 to Hubbell et al., all of which are hereby incorporated herein by reference.

Preferred monomers are the crosslinkable, biodegradable, water-soluble macromers described in U.S. Pat. No. 5,410, 016 to Hubbell et al. These monomers are characterized by having at least two polymerizable groups, separated by at least one degradable region. When polymerized in water, they form coherent gels that persist until eliminated by self-degradation. In the most preferred embodiment, the macromer is formed with a core of a polymer that is water soluble and biocompatible, such as the polyalkylene oxide polyethylene glycol, flanked by hydroxy acids such as lactic acid, having acrylate groups coupled thereto. Preferred monomers, in addition to being biodegradable, biocompatible, and non-toxic, also will be at least somewhat elastic after polymerization or curing.

It has been determined that monomers with longer distances between crosslinks are generally softer, more compliant, and more elastic. Thus, in the polymers of Hubbell, et al., increased length of the water-soluble segment, such as polyethylene glycol, tends to enhance elasticity. Molecular weights in the range of 10,000 to 35,000 of polyethylene glycol are preferred for such applications, although ranges from 3,000 to 100,000 also are useful.

In addition, coatings formed in accordance with the methods of the present invention may be formed as laminates (i.e., having multiple layers). Thus, for example, a lower layer of the laminate may consist of a more tightly crosslinked hydrogel that provides good adherence to the tissue surface and serves as a substrate for an overlying compliant coating to reactively bond thereto. Materials having lower molecular weights between crosslinks may be suitable for use as a base coating layer. Molecular weights in the range of 400 to 20,000 of polyethylene glycol are preferred for such applications, although ranges from 400 to 10,000 are more preferable.

It should be understood, however, that hydrogels that crosslink by a variety of other mechanisms, for example, by interaction of electrophilic and nucleophilic functional groups, also may be advantageously used in accordance with the principles of certain embodiments of the present invention.

Metal ions may be used either as an oxidizer or a reductant in redox initiating systems. For example, in the Example set forth hereinbelow, ferrous ions are used in combination with a peroxide or hydroperoxide to initiate polymerization, or as parts of a polymerization system. In this case, the ferrous ions serve as a reductant. In other previously known initiating systems, metal ions serve as an oxidant.

For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthamides and actinides, which have at least two readily accessible oxidation states.

Preferred metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide, etc., may be used.

Thermal initiating systems may be used rather than the redox-type systems described hereinabove. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Preferred macromers for use in forming tissue coatings using the apparatus of the present invention include any of a variety of in situ crosslinkable macromers that form hydrogel compositions in vivo. These macromers may, for example, be selected from compositions that are biodegradable, crosslinkable, and substantially water soluble macromers comprising at least one water soluble region, at least one degradable region, and statistically more than 1 polymerizable region on average per macromer chain, wherein the polymerizable regions are separated from each other by at least one degradable region. Alternatively, if biodegradability is not desirable, compositions that do not contain the biodegradable segments but are substantially water soluble and crosslink in vivo under acceptable physiological conditions may be used.

Referring now to FIGS. 15A, 15B and 15C, an illustrative embodiment of a sprayer constructed in accordance with the principles of the present invention is described. Sprayer 2010 comprises body 2011 having elongated barrel 2012, syringes 2013 and 2014, actuator 2015 and gas inlet port 2016 coupled to compressor 2017 via flexible hose 2018. Distal end 2019 of sprayer 2010 includes outlet nozzles 2020a and 2020b surrounded by gas flow outlets 2021a and 2021b, respectively. Compressor 2017 supplies a gas flow, preferably compressed air or carbon dioxide, to sprayer 2010 either continuously, or when activated by footpedal 2022. Gas inlet port 2016 may include filter 2016a to remove particulate contaminants, including bacteria and other microorganisms, from the gas flow.

Body 2011 includes compartments 2023 into which syringes 2013 and 2014 are placed so that the outlets of the syringes are coupled in fluid communication with the interior of tubes 2024 and 2025, respectively. Each of syringes 2013 and 2014 includes plunger 2026 that may be engaged in recesses 2027 of actuator 2015. Accordingly, when actuator 2015 is depressed, an equal volume of crosslinkable solution is dispensed from each of syringes 2013 and 2014. Alternatively, for some systems it may be desirable to omit actuator 2015 and instead spray the crosslinkable solutions onto the tissue in a sequential fashion. In either case, sterile crosslinkable solutions may be stored separately in syringes 2013 and 2014, and assembled in sprayer 2010 as required for a particular application.

Tube 2024 extends from the proximal end of barrel 2012, where it is coupled to syringe 2013, to a point a slightly beyond distal endface 2028 of barrel 2012, where it forms outlet nozzle 2020a. Tube 2024 is disposed within lumen 2029 that communicates with gas inlet port 2016. Gas entering sprayer 2010 via gas inlet port 2016 flows through the annular space defined by the exterior of tube 2024 and the interior surface of lumen 2029, exiting sprayer 2010 through gas flow outlet 2021a. As the gas, preferably air or carbon dioxide, flows through gas flow outlet 2021a, it mixes with the crosslinkable solution from syringe 2013 passing through outlet nozzle 2020a, breaking the crosslinkable solution into fine droplets or a mist.

Likewise, tube 2025 extends from the proximal end of barrel 2012, where it is coupled to syringe 2014, to a point a slightly beyond distal endface 2028 of barrel 2012, where it forms outlet nozzle 2020b. Tube 2025 is disposed within lumen 2030 that communicates with gas inlet port 2016. Thus, gas entering sprayer 2010 via gas inlet port 2016 flows through the annular space defined by the exterior of tube 2025 and the interior surface of lumen 2030, exiting sprayer 2010 through gas flow outlet 2021b. As the gas flows through gas flow outlet 2021b, it mixes with the crosslinkable solution from syringe 2014 passing through outlet nozzle 2020b, also breaking the crosslinkable solution into fine droplets or a mist.

Outlet nozzles 2020a and 2020b are preferably arranged so that the crosslinkable droplets or mist formed by outlet nozzle 2020a and gas flow outlet 2021a converges with that formed by outlet nozzle 2020b and gas flow outlet 2021b to provide a spray containing a mixture of the two crosslinkable solutions. As described hereinabove, the two solutions may either crosslink on contact within the spray, or crosslink upon contacting the tissue. Outlet nozzles 2020a and 2020b may extend several millimeters beyond distal endface 2028 of barrel 2012 to prevent clogging of the nozzles by premature crosslinking of the emergent fluids by cross-contamination.

Alternatively, it may be desirable to have outlet nozzles 2020a and 2020b approximately even with distal endface 2028 of barrel 2012 to reduce the gas flow rate required to entrain and atomize the solutions. Accordingly, outlet nozzles 2020a and 2020b and gas flow outlets 2021a and 2021b may be configured so that the movement of the gas flows from gas flow outlets 2021a and 2021b cause the crosslinkable solutions to be drawn out of nozzles 2020a and 2020b and entrained in the gas flows by a Venturi effect. In this case, no manual actuation or compression of the crosslinkable solutions is required, and plungers 2026 and actuator 2015 may be omitted. As a further alternative, instead of using footpedal 2022 to regulate the gas flow, compressor 2017 may be regulated with a valve (not shown) disposed on body 2011 or barrel 2012, that selectively diverts gas flow from lumens 2029 and 2030. This feature may be particularly useful when the sprayer is used in closed relatively fluid tight cavities, such as the pneumoperitoneum created during laparoscopic or pelvic surgery.

Body 2011, barrel 2012 and actuator 2015 preferably are constructed from a plastic such a polyethylene, while tubes 2024 and 2025 preferably comprise a rigid material, such as stainless steel. Syringes 2013 and 2014 may comprise materials typically used in medical devices, while compressor 2017 and flexible hose 2018 may be of the type commercially available, for example, that are used with airbrushes.

In operation, sprayer 2010 is coupled to compressor 2017 via flexible hose 2018. Syringes 2013 and 2014 are inserted into compartments 2023 of body 2011 and plungers 2026 of syringes 2013 and 2014 are engaged in recesses 2027 in actuator 2015. Distal end 2019 of sprayer 2010 is disposed within a body cavity, for example, intraoperatively in the abdomen or laparoscopically in the pneumoperitoneum, a few inches from tissue to be coated. Footpedal 2022 is then depressed to activate compressor 2017, while actuator 2015 is depressed to dispense crosslinkable solutions from outlet nozzles 2020a and 2020b. As the solutions emerge from nozzles 2020a and 2020b, they are atomized and partially or completely mixed, and directed onto the tissue to be coated. As a result of crosslinking, for example, induced by free radical or chemical crosslinking, the solutions form a film that adheres to the tissue to provide a therapeutic benefit. Alternatively, the solutions may be mixed when they contact the tissue surface.

In FIG. 15D, an alternative embodiment is depicted in which barrel 2012' includes outlet nozzles 2020a' and 2020b' disposed within single gas flow outlet 2021a' and gas flow lumen 2029'. Operation of this alternative embodiment is similar to that described hereinabove, except that the crosslinkable solutions are entrained from outlet nozzles 2020a' and 2020b' by a single stream of gas exiting gas flow outlet 2021a'. In addition, the sprayer may include a valve or valves (not shown) for regulating the amount of crosslinkable solution and gas existing outlet nozzles 2020a', 2020b' and 2021a', respectively. Such valves also may permit a jet of gas to be directed onto a targeted tissue, for example, to displace saline or body fluids to dry or clean the target tissue prior to instillation of the hydrogel barrier.

Certain embodiments include combining a suction-irrigation apparatus with an MIS system or precursor delivery device. An advantage of such a combination is that the tissue can be cleansed of clotted blood and adhesioniogenic materials and allows placement of a hydrogel barrier with a single device.

Functional Groups

Each precursor is multifunctional, meaning that it comprises two or more functional groups. In the case of precursors having electrophilic or nucleophilic functional groups, a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products. Such reactions are referred to as "crosslinking reactions".

Preferably, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di-or multifunctional poly(ethylene glycol) ("PEG") can be used.

Water Soluble Cores

The precursors preferably have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); dextran and proteins such as albumin. The polyethers and more particularly poly(oxyalkylenes) or poly(ethylene glycol) or polyethylene glycol are especially preferred. When the core is small molecular in nature, any of a variety of hydrophilic functionalities can be used to make the precursor water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

Biodegradable Linkages

If it is desired that the biocompatible crosslinked polymer be biodegradable or absorbable, one or more precursors having biodegradable linkages present in between the functional groups may be used. The biodegradable linkage optionally also may serve as the water soluble core of one or more of the precursors. In the alternative, or in addition, the functional groups of the precursors may be chosen such that the product of the reaction between them results in a biodegradable linkage. For each approach, biodegradable linkages may be chosen such that the resulting biodegradable biocompatible crosslinked polymer will degrade or be absorbed in a desired period of time. Preferably, biodegradable linkages are selected that degrade under physiological conditions into non-toxic products.

The biodegradable linkage may be chemically or enzymatically hydrolyzable or absorbable. Illustrative chemically hydrolyzable biodegradable linkages include polymers, copolymers and oligomers of glycolide, dl-lactide, l-lactide, caprolactone, dioxanone, trimethylene carbonate, carboxylate esters, phosphate esters, acetals, imines, and orthoesters. Illustrative enzymatically hydrolyzable biodegradable linkages include peptidic linkages cleavable by metalloproteinases and collagenases, and oligonucleotides cleavable by RNAses and DNAses. Additional illustrative biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

Visualization Agents

Where convenient, the biocompatible crosslinked polymer or precursor solutions (or both) may contain visualization agents to improve their visibility during surgical procedures. Visualization agents are especially useful when used in MIS procedures, due among other reasons to their improved visibility on a color monitor.

Visualization agents may be selected from among any of the various non-toxic colored substances suitable for use in medical implantable medical devices, such as FD&C blue dyes 1, 2 (indigo carmine), 3 and 6, eosin, methylene blue, indocyanine green, or colored dyes normally found in synthetic surgical sutures. The preferred color is green or blue because it has better visibility in presence of blood or on a pink or white tissue background. Red is the least preferred color, when used on a highly vascularized tissue that is red in color. However, red may be suitable when the underlying tissue is white, for example the cornea.

The visualization agent may be present with either reactive precursor species, e.g., a crosslinker or functional polymer solution. The preferred colored substance may or may not become chemically bound to the hydrogel.

The visualization agent may be used in small quantities, preferably less than 1% weight/volume, more preferably less than 0.05% weight/volume and most preferably less than 0.02% weight/volume concentration.

Additional visualization agents may be used, such as fluorescent (e.g., green or yellow fluorescent under visible light) compounds (e.g., fluorescein or eosin), x-ray contrast agents (e.g., iodinated compounds) for visibility under x-ray imaging equipment, ultrasonic contrast agents, or MRI contrast agents (e.g., Gadolinium containing compounds).

Visually observable visualization agents are preferred. Wavelengths of light from about 400 to 750 nm are observable to the human as colors (R. K. Hobbie, Intermediate Physics for Medicine and Biology, $2^{nd}$ Ed., pages 371-373). Blue color is perceived when the eye receives light that is predominantly from about 450 to 500 nm in wavelength and green is perceived at about 500 to 570 nm (Id.). The color of an object is therefore determined by the predominant wavelength of light that it reflects or emits. Further, since the eye detects red or green or blue, a combination of these colors may be used to simulate any other color merely by causing the eye to receive the proportion of red, green, and blue that is perceived as the desired color by the human eye. Blue and green visualization agents are preferred since they are most readily visible when observing in situ crosslinking due to the approximately red color of the background color of tissue and blood. The color blue, as used herein, means the color that is perceived by a normal human eye stimulated by a wavelength of about 450 to 500 nm and the color green, as used herein, means the color that is perceived by a normal human eye stimulated by a wavelength of about 500 to 570 nm.

Crosslinking Reactions

The crosslinking reactions preferably occur in aqueous solution under physiological conditions. More preferably the crosslinking reactions occur "in situ", meaning they occur at local sites such as on organs or tissues in a living animal or human body. More preferably the crosslinking reactions do not release heat of polymerization. Preferably the crosslinking reaction leading to gelation occurs within about 10 minutes, more preferably within about 2 minutes, more preferably within about one minute, and most preferably within about 30 seconds. When it is desirable to build up a coating on a convex surface, the crosslinking reaction preferably occurs within about 2 minutes, more preferably in 30-60 seconds, and most preferably in 2-4 seconds.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Several methods for activating such functional groups are known in the art. Preferred activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide groups are the most preferred groups for crosslinking of proteins or amine functionalized polymers such as amino terminated polyethylene glycol ("APEG").

FIGS. 1 to 5 illustrate various embodiments of preferred crosslinkers and functional polymers.

FIG. 1 illustrates possible configurations of degradable electrophilic crosslinkers or functional polymers. The biodegradable regions are represented by (˜˜˜˜˜˜); the functional groups are represented by (<) and the inert water soluble cores are represented by (–). For crosslinkers, the central core is a water soluble small molecule and for functional polymers the central core is a water soluble polymer of natural or synthetic origin.

When Structure A in FIG. 1 is a functional polymer, it is a linear water soluble and biodegradable functional polymer, end-capped with two functional groups (e.g., N-hydroxysuccinimide ester or NHS, epoxide or similar reactive groups). The water soluble core may be a polyalkylene oxide, preferably polyethylene glycol block copolymer, and it is extended with at least one biodegradable linkage between it and each terminal functional group. The biodegradable linkage may be a single linkage or copolymers or homopolymers of absorbable polymers such as polyhydroxy acids or polylactones.

When Structure B in FIG. 1 is a functional polymer it is a branched or star shaped biodegradable functional polymer which has an inert polymer at the center. Its inert and water soluble core is terminated with oligomeric biodegradable extensions, which in turn are terminated with reactive functional groups.

When Structures C and D in FIG. 1 are functional polymers, they are multifunctional 4 arm biodegradable functional polymers. This polymer again has a water-soluble soluble core at the center, which is a 4 arm, tetrafunctional polyethylene glycol (Structure C) or block copolymer of PEO-PPO-PEO such as Tetronic 908 (Structure D) which is extended with by small oligomeric extensions of biodegradable polymer to maintain water solubility and terminated with reactive functional end-groups such as CDI or NHS.

When Structure E in FIG. 1 is a functional polymer, it is a multifunctional star or graft type biodegradable polymer. This polymer has a water-soluble polymer like polyethylene oxide, polyvinyl alcohol or poly(vinyl pyrrolidinone) at the core which is completely or partially extended with biodegradable polymer. The biodegradable polymer is terminated with reactive end groups.

Structures A-E in FIG. 1 need not have polymeric cores and may be small molecule crosslinkers. In that case, the core may comprise a small molecule like ethoxylated glycerol, inositol, trimethylolpropane etc. to form the resultant crosslinker. In addition, Structures A-E in FIG. 1 need not have polymeric biodegradable extensions, and the biodegradable extensions may consist of small molecules like succinate or glutarate or combinations of 2 or more esters, such as glycolate/2-hydroxybutyrate or glycolate/4-hydroxyproline, etc. A dimer or trimer of 4-hydroxyproline may be used not only to add degradability, but also to add nucleophilic functional group reactive sites via the pendant primary amines which are part of the hydroxyproline moiety.

Other variations of the core, the biodegradable linkage, and the terminal electrophilic group in Structures A-E in FIG. 1 may be constructed, so long as the resulting functional polymer has the properties of low tissue toxicity, water solubility, and reactivity with nucleophilic functional groups.

FIG. 2 illustrates various embodiments of nucleophilic biodegradable water soluble crosslinkers and functional polymers suitable for use with electrophilic functional polymers and crosslinkers described herein.

The biodegradable regions are represented by (˜˜˜˜˜˜); the functional groups are represented by (|); and the inert water soluble cores are represented by (–). For crosslinkers, the central core is a water soluble small molecule and for functional polymers the central core is a water soluble polymer of natural or synthetic origin.

When Structure F in FIG. 2 is a functional polymer, it is a linear water soluble biodegradable polymer terminated with reactive functional groups like primary amine. The linear water-soluble core is a polyalkylene oxide, preferably polyethylene glycol block copolymer, which is extended with the biodegradable region which is a copolymer or homopolymers of polyhydroxy acids or polylactones. This biodegradable polymer is terminated with primary amines.

When Structure G in FIG. 2 is a functional polymer, it is a branched or star shaped biodegradable polymer which has an inert polymer at the center. The inert polymer is extended with single or oligomeric biodegradable extensions which are terminated with reactive functional groups.

When Structures H and I in FIG. 2 are functional polymers, they are multifunctional 4 arm biodegradable polymers. These polymers again have water-soluble cores at their center which are either a 4 arm, tetrafunctional polyethylene glycol (Structure H) or a block copolymer of PEO-PPO-PEO such as Tetronic 908 (Structure I), extended with small oligomeric extensions of biodegradable polymers to maintain water solubility, and terminated with functional groups such as amines and thiols.

When Structure J in FIG. 2 is a functional polymer, it is a multifunctional star or graft type biodegradable polymer. This polymer has a water soluble polymer like polyethylene oxide, polyvinyl alcohol or poly(vinyl pyrrolidinone) at the core which is completely or partially extended with biodegradable polymer. The biodegradable polymer is terminated with reactive end groups.

Structures F-J in FIG. 2 need not have polymeric cores and may be small molecule crosslinkers. In that case, the core may comprise a small molecule like ethoxylated glycerol, inositol, trimethylolpropane etc. to form the resultant crosslinker.

Other variations of the core, the biodegradable linkage, and the terminal nucleophilic functional group in Structures F-J in FIG. 2 may be constructed, so long as the resulting functional polymer has the properties of low tissue toxicity, water solubility, and reactivity with electrophilic functional groups.

FIG. 3 illustrates configurations of water-soluble electrophilic crosslinkers or functional polymers where the core is biodegradable. The biodegradable regions are represented by (˜˜˜˜˜˜) and the functional groups are represented by (<). The biodegradable core is terminated with a reactive functional group that is also water solubilizing, such a N-hydroxysulfosuccinimide ester ("SNHS") or N-hydroxyethoxylated succinimide ester ("ENHS").

Structure K in FIG. 3 depicts a difunctional biodegradable polymer or oligomer terminated with SNHS or ENHS. The oligomers and polymers may be made of a poly(hydroxy acid) such as poly(lactic acid), which is insoluble in water. However, the terminal carboxylic acid group of these oligomers or polymers can be activated with N-hydroxysulfosuccinimide ester ("SNHS") or N-hydroxyethoxylated succinimide ester ("ENHS") groups. An ionic group, like a metal salt (preferably sodium salt) of sulfonic acid, or a nonionic group, like a polyethylene oxide on the succinimide ring, provides water-solubility while the NHS ester provides chemical reactivity towards amines. The sulfonate groups (sodium salts) or ethoxylated groups on the succinimide ring solubilize the oligomer or polymer without appreciably inhibiting reactivity towards amine groups.

Structures L-0 in FIG. 3 represent multi-branched or graft type structures with terminal SNHS or ENHS group. The cores may comprise various non-toxic polyhydroxy compounds like sugars (xylitol, erythritol), glycerol, trimethylolpropane, which have been reacted with anhydrides such as succinic or glutaric anhydrides. The resultant acid groups were then activated with SNHS or ENHS groups to form water soluble crosslinkers or functional polymers.

FIG. 4 illustrates various nucleophilic functional polymers or crosslinkers that are not biodegradable. The nucleophilic functional groups are represented by (|) and the inert water-soluble cores are represented by (–). For crosslinkers, the central core is a water-soluble small molecule and for functional polymers the central core is a water soluble polymer of natural or synthetic origin.

When Structure P in FIG. 4 is a functional polymer it may be a water-soluble linear polymer such as polyethylene glycol terminated with reactive end group such as primary amines and thiols. Such polymers are commercially available from Sigma (Milwaukee, Wis.) and Shearwater Polymers (Huntsville, Ala.). Some other preferred difunctional polymers are PPO-PEO-PPO block copolymers such as Pluronic F68 terminated with amine groups. Pluronic or Tetronic polymers are normally available with terminal hydroxyl groups. The hydroxyl groups are converted into amine groups by methods known in the art.

When Structures Q-T in FIG. 4 are functional polymers they may be multifunctional graft or branch type water soluble copolymers with terminal amine groups.

Structures P-T in FIG. 4 need not have polymeric cores and may be small molecule crosslinkers. In that case, the core may comprise a small molecule like ethoxylated glycerol, inositol, trimethylolpropane, dilysine etc. to form the resultant crosslinker.

Other variations of the core and the terminal nucleophilic functional group in Structure P-T in FIG. 4 may be employed, so long as the properties of low tissue toxicity, water solubility, and reactivity with electrophilic functional groups are maintained.

FIG. 5 illustrates various electrophilic functional polymers or crosslinkers that are not biodegradable. The electrophilic functional groups are represented by (<) and the inert water soluble cores are represented by (–). For crosslinkers, the central core is a water soluble small molecule and for functional polymers the central core is a water soluble polymer of natural or synthetic origin.

When Structure U is a functional polymer, it may be a water-soluble polymer such as polyethylene glycol terminated reactive end group such as NHS or epoxide. Such polymers are commercially available from Sigma and Shearwater polymers. Some other preferred polymers are PPO-PEO-PPO block copolymers such as Pluronic F68 terminated with NHS or SNHS group. Pluronic or Tetronic polymers are normally available with terminal hydroxyl groups. The hydroxyl groups are converted into acid group by reacting with succinic anhydride. The terminated acid groups are reacted with N-hydroxysuccinimide in presence of DCC to generate NHS activated Pluronic polymer.

When Structures V-Y are functional polymers they may be multifunctional graft or branch type PEO or PEO block copolymers (Tetronics) activated with terminal reactive groups such as NHS.

Structures U-Y in FIG. 5 need not have polymeric cores and may be small molecule crosslinkers. In that case, the core may comprise a small molecule like ethoxylated glycerol, tetraglycerol, hexaglycerol, inositol, trimethylolpropane, dilysine etc. to form the resultant crosslinker.

Other variations of the core and the terminal nucleophilic functional group in Structures U-Y in FIG. 5 may be employed, so long as the properties of low tissue toxicity, water solubility, and reactivity with electrophilic functional groups are maintained.

Preparation of Structures A-Y in FIGS. 1-5

The polymeric crosslinkers and functional polymers illustrated as Structures A-Y in FIGS. 1 to 5 may be prepared using variety of synthetic methods. Their preferred compositions are described in Table 1.

TABLE 1

Preferred Crosslinkers and Functional Polymers

| Structure | Brief Description | Typical Example |
| --- | --- | --- |
| A | Water soluble, linear difunctional crosslinker or functional polymer with water soluble core, extended with biodegradable regions such as oligomers of hydroxyacids or peptide sequences which are cleavable by enzymes and terminated with protein reactive functional groups | Polyethylene glycol or ethoxylated propylene glycol chain extended with oligolactate and terminated with N-hydroxysuccinimide esters |
| B | Water soluble, trifuncational crosslinker or functional polymer with water soluble core, extended with biodegradable regions such as oligomers of | Ethoxylated glycerol chain extended with oligolactate and terminated with N-hydroxysuccinimide esters |

TABLE 1-continued

Preferred Crosslinkers and Functional Polymers

| Structure | Brief Description | Typical Example |
|---|---|---|
| | hydroxyacids or peptide sequences and terminated with protein reactive functional groups | |
| C | Water soluble, tetrafunctional crosslinker or functional polymer with water soluble core, extended with biodegradable regions such as oligomers of hydroxyacids or peptide sequences and terminated with protein reactive functional groups | 4 arm polyethylene glycol, erythritol or pentaerythritol or pentaerythritol chain extended with oligolactate and terminated with N-hydroxysuccinimide esters |
| D | Water soluble, tetrafunctional crosslinker or functional polymer with water soluble core, extended with biodegradable regions such as oligomers of hydroxyacids or peptide sequences and terminated with protein reactive functional groups | Ethoxylated ethylene diamine or polyethylene oxide-polypropylene oxide-polyethylene oxide block copolymer like Tetronic 908 chain extended with oligotrimethylene carbonate and terminated with N-hydroxysuccinimide ester |
| E | Water soluble, branched crosslinker or functional polymer with water soluble core, extended with biodegradable regions such as oligomers of hydroxyacids or peptide sequences and terminated with protein reactive functional groups | Low molecular weight polyvinyl alcohol with 1% to 20% hydroxyl groups extended with oligolactate and terminated with N-hydroxysuccinimide ester |
| F | Water soluble, liner difunctional crosslinker or functional polymer with water soluble core, extended with biodegradable regions such as oligomers of hydroxyacids or peptide sequences and terminated with amines, carboxylic acid or thiols | Polyethylene oxide-polypropylene oxide-polyethylene oxide block copolymer surfactant like Pluronic F68 chain extended with oligolactate and terminated with amino acids such as lysine or peptide sequences that may contain two amine groups |
| G | Water soluble, trifunctional crosslinker or functional polymer with water soluble core, extended with biodegradable regions such as oligomers of hydroxyacids or peptide sequences and terminated with amines, carboxylic acid or thiols | Ethoxylated glycerol chain extended with oligolactate and terminated with aminoacid such as lysine |
| H | Water soluble, tetrafuncational crosslinker or functional polymer with water soluble core, extended with biodegradable regions such as oligomers of hydroxyacids or peptide sequences and terminated with amines, carboxylic acid or thiols | 4 arm polyethylene glycol or tetra erythritol chain extended with oligolactate and terminated with aminoacid such as lysine |
| I | Water soluble, tetrafunctional crosslinker or functional polymer with water soluble core, extended with biodegradable regions such as oligomers of hydroxyacids or peptide sequences and terminated with amines, carboxylic acid or thiols | Ethoxylated ethylene diamine or polyethylene oxide-polypropylene oxide-polyethylene oxide block copolymer like Tetronic 908 chain extended with oligotrimethylene carbonate and terminated with aminoacid such as lysine |
| J | Water soluble, multifunctional or graft type crosslinker or functional polymer with water soluble core, extended with biodegradable regions such as oligomers of hydroxyacids or peptide sequences and terminated with amines, carboxylic acid or thiols | Low molecular weight polyvinyl alcohol with 1-20% hydroxyl groups extended with oligolactate and terminated with aminoacid such as lysine |
| K | Water soluble, linear difunctional crosslinker or functional polymer such as | Difunctional oligolactic acid with terminal carboxyl groups which are activated with n- |

TABLE 1-continued

Preferred Crosslinkers and Functional Polymers

| Structure | Brief Description | Typical Example |
|---|---|---|
| | oligomers of hydroxyacids or peptide sequences which are terminated with protein reactive functional groups | hydroxysulfosuccinimi de ester or ethoxylated n-hydroxysuccinimide ester. |
| L | Water soluble branched trifunctional crosslinker or functional polymer such as oligomers of hydroxyacids or peptide sequences which are terminated with protein reactive functional groups | Trifunctional oligocaprolactone with terminal carboxyl groups which are activated with n-hydroxysulfosuccinimi de ester or ethoxylated n-hydroxysuccinimide ester. |
| M | Water soluble, branched tetrafunctional crosslinker or functional polymer such as oligomers of hydroxyacids or peptide sequences which are terminated with protein reactive functional groups | Tetrafunctional oligocaprolactone with terminal carboxyl groups which are activated with n-hydroxysulfosuccinimi de ester or ethoxylated n-hydroxysuccinimide ester. |
| N | Water soluble, branched tetrafunctional crosslinker or functional polymer such as oligomers of hydroxyacids or peptide sequences which are terminated with protein reactive functional groups | Tetrafunctional oligocaprolatone with terminal carboxyl groups which are activated with n-hydroxysulfosuccinimide ester or ethoxylated n-hydroxysuccinimide ester. |
| O | Water soluble, branched multifunctional crosslinker or functional polymer such as oligomers f hydroxyacids or peptide sequences which are terminated with protein reactive functional groups | Multifunctional oligolactic acid with terminal carboxyl groups which are activated with n-hydroxysulfosuccinimide ester or ethoxylated n-hydroxysuccinimide ester. |
| P | Water soluble, linear difunctional crosslinker or functional polymer terminated with amines, carboxylic acid or thiols functional groups | Polyethylene glycol with terminal amines groups |
| Q | Water soluble, branched trifunctional crosslinker or functional polymer terminated with amines, carboxylic acid or thiols as functional group | Ethoxylated glycerol with terminal amines groups |
| R | Water soluble, branched tetrafunctional crosslinker of functional polymer terminated with amines, carboxylic acid or thiols functional groups | 4 arm polyethylene glycol modified to produce terminal amine groups |
| S | Water soluble, branched tetrafunctional crosslinker or functional polymer terminated with amines, carboxylic acid or thiols functional groups | Ethoxylated ethylene diamine or polyethylene oxide-polyprophylene oxide-polyethylene oxide block copolymer like Tetronic 908 modified to generate terminal amine groups |
| T | Water soluble, branched or graft crosslinker or functional polymer with terminal amines, carboxylic acid or thiols functional groups | Polylysine, albumin, polyallyl amine |
| U | Water soluble, linear difunctional crosslinker or functional polymer terminated with protein reactive functional groups | Polylysine, albumin, polyallyl amine |
| V | Water soluble branched trifunctional crosslinker or functional polymer terminated with protein reactive functional groups | Ethoxylated glycerol terminated with n-hydroxysuccinimide |
| W | Water soluble branched tetrafunctional crosslinker or functional polymer terminated with protein reactive functional groups | 4 arm polyethylene glycol terminated with n-hydroxysuccinimide esters |
| X | Water soluble branched tetrafunctional crosslinker or functional polymer terminated | Ethoxylated ethylene diamine or polyethylene oxide-polypropylene oxide-polyethylene oxide block |

TABLE 1-continued

Preferred Crosslinkers and Functional Polymers

| Structure | Brief Description | Typical Example |
|---|---|---|
|  | with protein reactive functional groups, also, optionally with degradable feature | copolymer like Tetronic 908 with n-hydroxysuccinimide ester as end group; also, 4 arm polyethylene glycol extended with carboxymethyl hydroxy butyric acid ester terminated with n-hydroxysuccinimide esters |
| Y | Water soluble, branched or graft polymer crosslinker or functional polymer with protein reactive functional groups | Poly (vinyl pyrrolidinone)-co-poly (n-hydroxysuccinimide acrylate) copolymer (9:1), molecular weight <40000 Da |

First, the biodegradable links of Structures A-J in FIGS. 1 and 2 may be composed of specific di or multifunctional synthetic amino acid sequences which are recognized and cleaved by enzymes such as collagenase, and may be synthesized using methods known to those skilled in the peptide synthesis art. For example, Structures A-E in FIG. 1 may be obtained by first using carboxyl, amine or hydroxy terminated polyethylene glycol as a starting material for building a suitable peptide sequence. The terminal end of the peptide sequence is converted into a carboxylic acid by reacting succinic anhydride with an appropriate amino acid. The acid group generated is converted to an NHS ester by reaction with N-hydroxysuccinimide.

The functional polymers described in FIG. 2 may be prepared using a variety of synthetic methods. In a preferred embodiment, the polymer shown as Structure F may be obtained by ring opening polymerization of cyclic lactones or carbonates initiated by a dihydroxy compound such as Pluronic F 68 in the presence of a suitable catalyst such as stannous 2-ethylhexanoate. The molar equivalent ratio of caprolactone to Pluronic is kept below 10 to obtain a low molecular weight chain extension product so as to maintain water solubility. The terminal hydroxyl groups of the resultant copolymer are converted into amine or thiol by methods known in the art.

In a preferred method, the hydroxyl groups of a Pluronic-caprolactone copolymer are activated using tresyl chloride. The activated groups are then reacted with lysine to produce lysine terminated Pluronic-caprolactone copolymer. Alternatively, an amine-blocked lysine derivative is reacted with the hydroxyl groups of a Pluronic-caprolactone copolymer and then the amine groups are regenerated using a suitable deblocking reaction.

Structures G, H, I and J in FIG. 2 may represent multifunctional branched or graft type copolymers having water soluble core extended with oligohydroxy acid polymer and terminated with amine or thiol groups.

Figure 6:
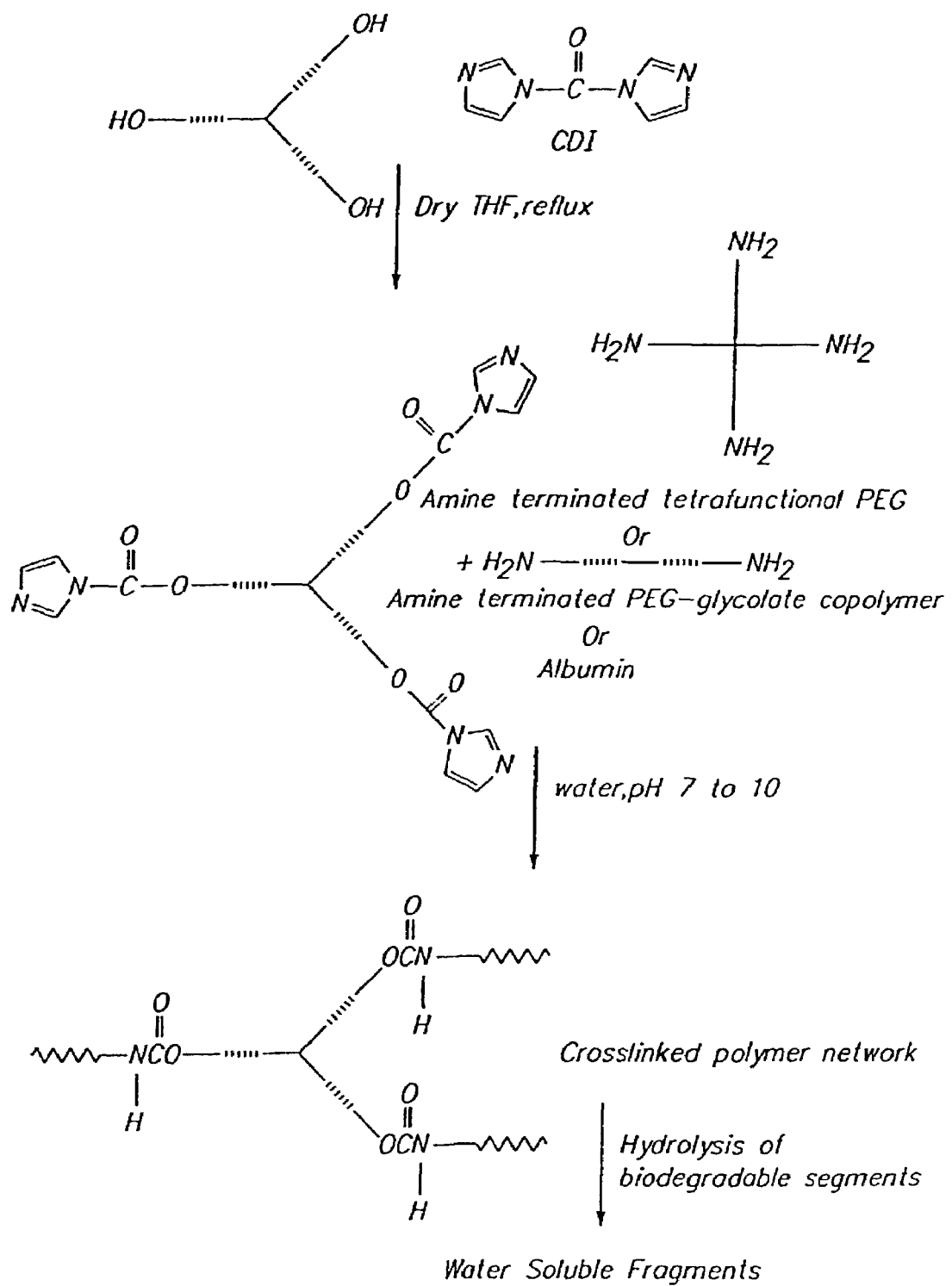
FIG. 6 depicts the preparation of an electrophilic water soluble crosslinker or functional polymer using carbodiimide ("CDI") activation chemistry, its crosslinking reaction with a nucleophilic water soluble functional polymer to form a biocompatible crosslinked polymer product, and the hydrolysis of that biocompatible crosslinked polymer to yield water soluble fragments.

For example, in a preferred embodiment, the functional polymer illustrated as Structure G in FIG. 2 is obtained by ring opening polymerization of cyclic lactones or carbonates initiated by a tetrahydroxy compound such as 4 arm, tetrahydroxy polyethylene glycol (molecular weight 10,000 Da), in the presence of a suitable catalyst such as stannous octoate. The molar equivalent ratio of cyclic lactone or carbonate to PEG is kept below 10 to obtain a low molecular weight extension, and to maintain water solubility (polymers of cyclic lactones generally are not as water soluble as PEG). Alternatively, hydroxyacid as a biodegradable link may be attached to the PEG chain using blocking/deblocking chemistry known in the peptide synthesis art. The terminal hydroxy groups of the resultant copolymer are activated using a variety of reactive groups known in the art. The CDI activation chemistry and sulfonyl chloride activation chemistry is shown in FIGS. 6 and 7, respectively.

Figure 8:
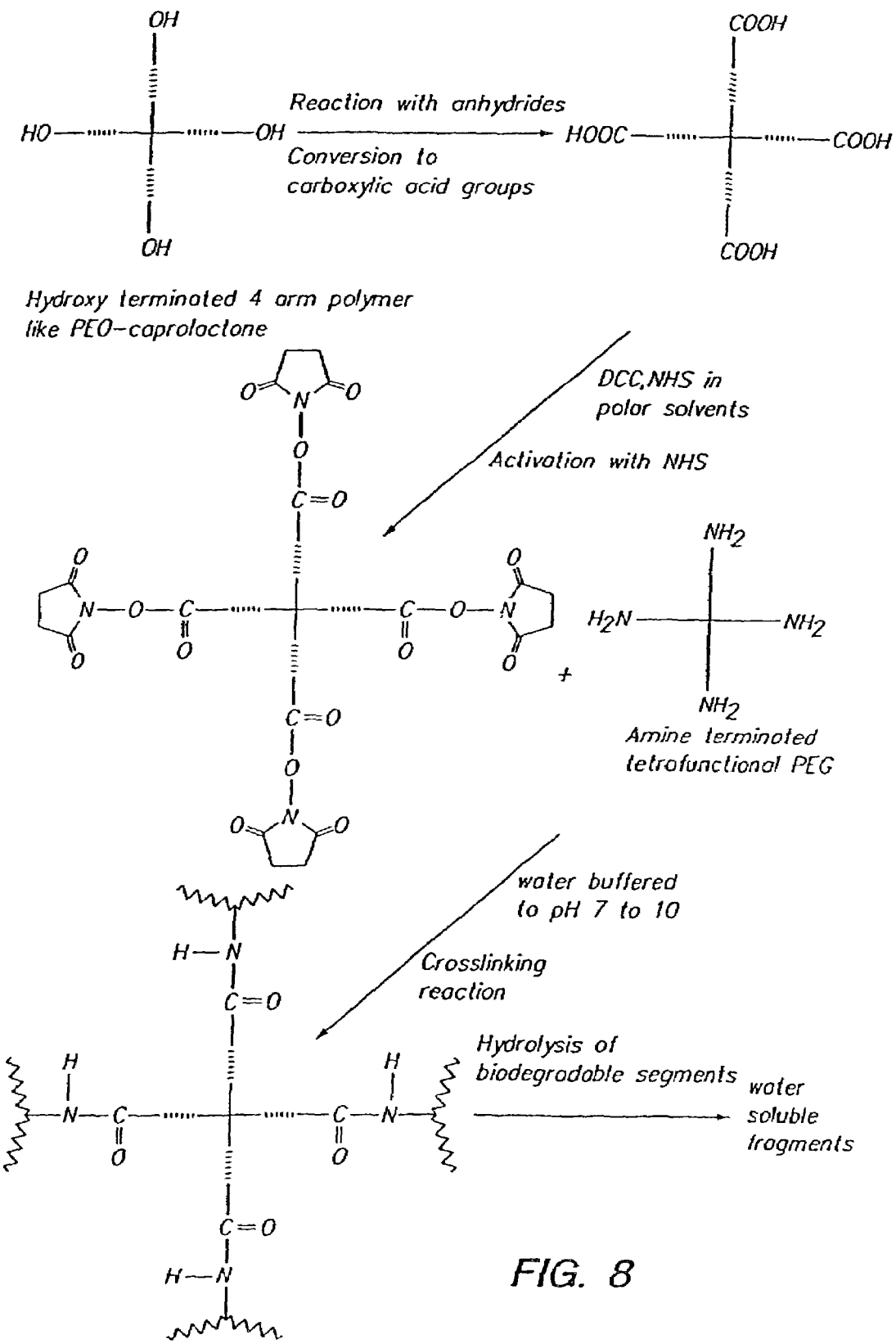
FIG. 8 depicts the preparation of an electrophilic water soluble crosslinker or functional polymer using N-hydroxysuccinimide ("NHS") activation chemistry, its crosslinking reaction with a nucleophilic water soluble functional polymer to form a biocompatible crosslinked polymer product, and the hydrolysis of that biocompatible crosslinked polymer to yield water soluble fragments.
Figure 10:
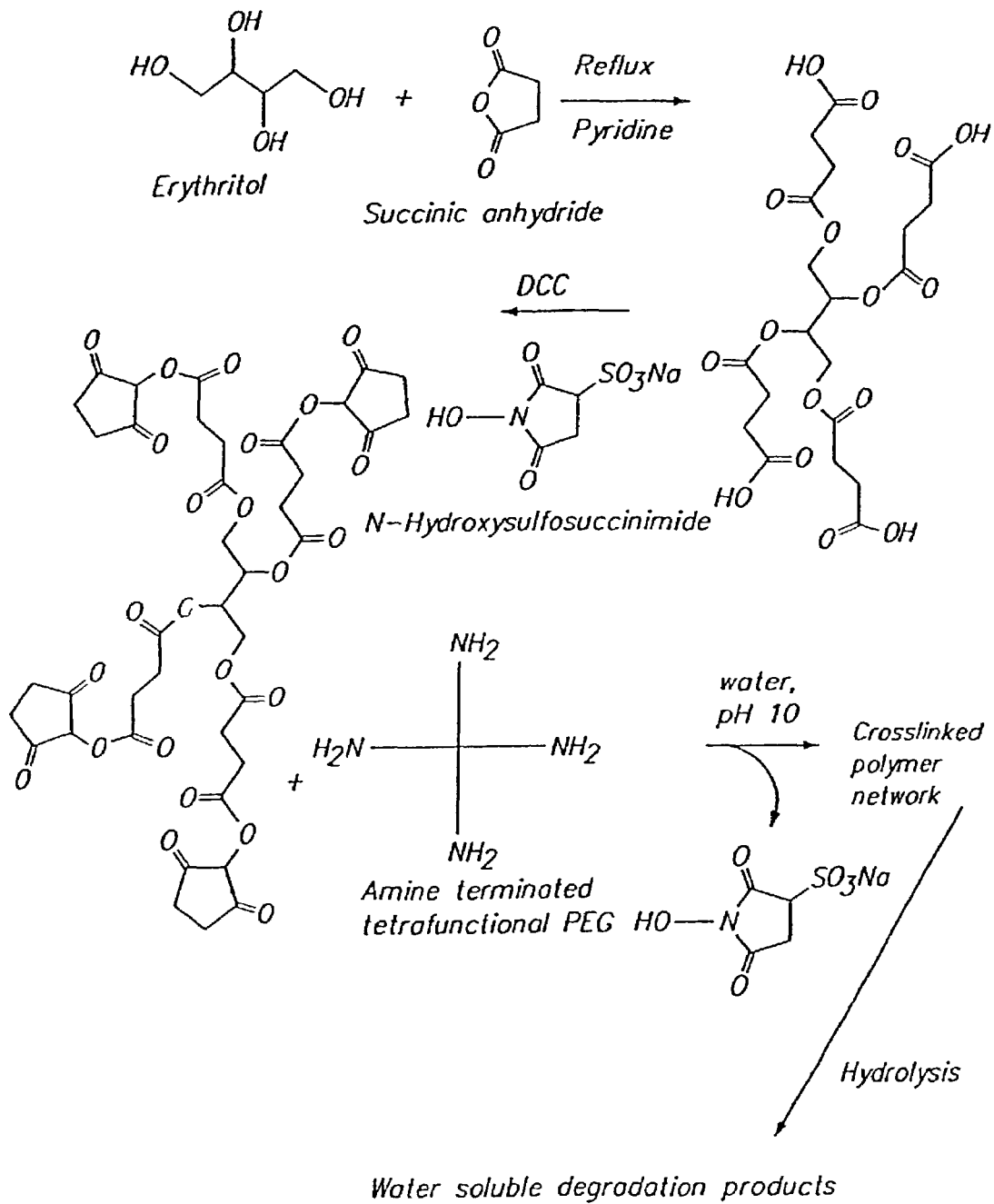
FIG. 10 shows the N-hydroxysulfosuccinimide ("SNHS") activation of a tetrafunctional sugar-based water soluble synthetic crosslinker and its crosslinking reaction with 4-arm amine terminated polyethylene glycol to form a biocompatible crosslinked polymer product, and the hydrolysis of that biocompatible crosslinked polymer to yield water soluble fragments.

The most preferred reactive groups are N-hydroxysuccinimide esters, synthesized by any of several methods. In a preferred method, hydroxyl groups are converted to carboxylic groups by reacting them with anhydrides such as succinic anhydride in the presence of tertiary amines such as pyridine or triethylamine or dimethylaminopyridine ("DMAP"). Other anhydrides such as glutaric anhydride, phthalic anhydride, maleic anhydride and the like may also be used. The resultant terminal carboxyl groups are reacted with N-hydroxysuccinimide in the presence of dicyclohexylcarbodiimide ("DCC") to produce N-hydroxysuccinimide ester (referred as NHS activation). The NHS activation and crosslinking reaction scheme is shown in FIG. 8. The most preferred N-hydroxysuccinimide esters are shown in FIG. 9.

In a preferred embodiment, the polymer shown as structure H is obtained by ring opening polymerization of glycolide or trimethylene carbonate initiated by a tetrahydroxy compound such as tetrafunctional polyethylene glycol (molecular weight 2000 Da) in the presence of a catalyst such as stannous 2-ethylhexoate. The molar equivalent ratio of glycolide to PEG is kept from 2 to 10 to obtain a low molecular weight extension. The terminal hydroxy groups of the resultant copolymer are converted into amine groups by reaction with lysine as mentioned previously. Similar embodiments can be obtained using analogous chain extension synthetic strategies to obtain structures F, G, I and J by starting with the appropriate corresponding polyol.

Structures K, L, M, N and O in FIG. 3 are made using a variety of synthetic methods. In a preferred embodiment, the polymer shown as Structure L in FIG. 3 is obtained by ring opening polymerization of cyclic lactones by a trihydroxy compound such as glycerol in the presence of a catalyst such as stannous 2-ethylhexanoate. The molar equivalent ratio of cyclic lactone to glycerol is kept below 2, so that only low molecular weight oligomers are obtained. The low molecular weight oligomer ester is insoluble in water. The terminal hydroxy groups of the resultant copolymer are activated using N-hydroxysulfosuccinimide groups. This is achieved by converting hydroxy groups to carboxylic groups by reacting with anhydrides such as succinic anhydride in presence of tertiary amines. The resultant terminal carboxyl groups are reacted with N-hydroxysulfosuccinimide or N-hydroxyethoxylated succinimide in the presence of dicyclohexylcarbodiimide ("DCC") to produce a sulfonated or ethoxylated NHS ester. The sulfonate or PEO chain on the succinimide ring gives water solubility to the oligoester.

The foregoing method generally is applied to solubilize only low molecular weight multi-branched oligoesters, with molecular weights below 1000. In another variation of this method, various non-toxic polyhydroxy compounds, preferably sugars, such as erythritol, xylitol are reacted with succinic anhydride in the presence of a tertiary amine. The terminal carboxyl group of succinated erythritol is esterified with N-hydroxysulfosuccinimide (FIG. 9). Similar embodiments may be obtained using analogous synthetic strategies to obtain structures K, and M-O by starting with the appropriate starting materials.

Structures P-R may be synthesized by reacting the appropriate starting material, such as a linear (P) or 2- or 3-arm branched PEG (Q, R) with hydroxy end groups, with lysine as mentioned previously, such that the arms of the PEG oligomers are capped with amine end groups. Structure S may be synthesized, using a multistep reaction, from PEG, glycerol and a diisocyanate. In the first step a PEG diol is reacted with excess diisocyanate, such as 4,4'diphenyl methane diiusocyanate ("MDI"), methylene-bis (4-cyclohexylisocyanate) ("HMDI") or hexamethylenediisocyanate ("HDI"). After purification the resultant PEG diisocyanate is added dropwise to excess glycerol or trimethylol propane or other triol and reacted to completion. The purified product, now having diol end groups, is again reacted with excess diisocyanate and purified, yielding a PEG-tetra-isocyanate. This tetrafunctional PEG subsequently may be reacted with excess PEG diols, yielding a 4 arm PEG synthesized from a PEG diol oligomer. In the final step lysine end groups are incorporated, as discussed previously.

Structure T may be synthesized as follows: First synthesize a random copolymer of PEG-monoacrylate and some other acrylate or combination of acrylates, such that the final polyacrylate is water soluble. Other acrylates include, but are not limited to, 2-hydroxyethylacrylate, acrylic acid, and acrylamide. Conditions may be varied to control the molecular weight as desired. In the final step, the acrylate is reacted with lysine as discussed previously, using an appropriate quantity to achieve the desired degree of amination.

One method of synthesizing Structures U-Y is to use dicyclohexylcarbodiimide coupling to a carboxylate end group. For Structures U-W, one can react the appropriate PEG-diol, -triol or -tetra-hydroxy starting material with excess succinic anhydride or glutaric anhydride such that all end groups are effectively carboxylated. Structures X and Y may be made in a manner similar to that used for Structures S and T, except that in the last step instead of end capping with lysine, end capping with succinic anhydride or glutaric anhydride is performed.

Preparation of Biocompatible Polymers

Several biocompatible crosslinked hydrogels may be produced using the crosslinkers and functional polymers described in FIGS. 1 to 5. Preferred combinations of such polymers suitable for producing such biocompatible crosslinked polymers are described in Table 2. In Table 2, the crosslinker functional groups are N-hydroxy succinimide esters and the functional polymer functional groups are primary amines.

TABLE 2

Biocompatible Polymers Synthesized from Crosslinkers and Functional Polymers of Table 1

| Crosslinker Structure | Functional Polymer Structure | Concentration | Medium |
| --- | --- | --- | --- |
| B or C | H and R | Molar Equivalent; >20% W/V | Borate or triethanol amine buffer, pH 7-10 |
| A, B or C | H, P, Q, R and S | Molar Equivalent; >20% W/V | Borate or triethanol amine buffer, pH 7-10 |
| Y | T, H, P and Q | Molar Equivalent; >10% W/V | Borate or triethanol amine buffer, pH 7-910 |
| W, V | H and J | Molar Equivalent; >20% W/V | Bicarbonate buffer, pH 7-10 |
| X | I, J and H | Molar Equivalent; >20% W/V | Borate or triethanol amine buffer, pH 7-10 |

The reaction conditions for crosslinking will depend on the nature of the functional groups. Preferred reactions are conducted in buffered aqueous solutions at pH 5 to 12. The preferred buffers are sodium borate buffer (pH 10) and triethanol amine buffer (pH 7). Suitable buffers are also sodium phosphate, carbonate, and potassium hydrogen phthalate. Elevated pH increases the speed of electrophilic-nucleophilic reactions. In some embodiments, organic solvents such as ethanol or isopropanol may be added to improve the reaction speed or to adjust the viscosity of a given formulation.

The synthetic crosslinked gels described above degrade due to hydrolysis of the biodegradable region. The degradation of gels containing synthetic peptide sequences will depend on the specific enzyme and its concentration. In some cases, a specific enzyme may be added during the crosslinking reaction to accelerate the degradation process.

When the crosslinker and functional polymers are synthetic (for example, when they are based on polyalkylene oxide), then it is desirable and in some cases essential to use molar equivalent quantities of the reactants. In some cases, molar excess crosslinker may be added to compensate for side reactions such as reactions due to hydrolysis of the functional group.

When choosing the crosslinker and crosslinkable polymer, at least one of polymers must have more than 2 functional groups per molecule and at least one degradable region, if it is desired that the resultant biocompatible crosslinked polymer be biodegradable. For example, the difunctional crosslinker shown as Structure A in FIG. 1 cannot form a crosslinked network with the difunctional polymers shown as Structure F in FIG. 2 or Structure P in FIG. 4. Generally, it is preferred that each biocompatible crosslinked polymer precursor have more than 2 and more preferably 4 or more functional groups.

Preferred electrophilic functional groups are NHS, SNHS and ENHS (FIG. 9). Preferred nucleophilic functional groups are primary amines. The advantage of the NHS-amine reaction is that the reaction kinetics lead to quick gelation usually within 10 about minutes, more usually within about 1 minute and most usually within about 10 seconds. This fast gelation is preferred for in situ reactions on live tissue.

The NHS-amine crosslinking reaction leads to formation of N-hydroxysuccinimide as a side product. The sulfonated or ethoxylated forms of N-hydroxysuccinimide are preferred due to their increased solubility in water and hence their rapid clearance from the body. The sulfonic acid salt on the succinimide ring does not alter the reactivity of NHS group with the primary amines.

The NHS-amine crosslinking reaction may be carried out in aqueous solutions and in the presence of buffers. The preferred buffers are phosphate buffer (pH 5.0-7.5). triethanolamine buffer (pH 7.5-9.0) and borate buffer (pH 9.0-12) and sodium bicarbonate buffer (pH 9.0-10.0).

Aqueous solutions of NHS based crosslinkers and functional polymers preferably are made just before the crosslinking reaction due to reaction of NHS groups with water. Longer "pot life" may be obtained by keeping these solutions at lower pH (pH 4-5).

The crosslinking density of the resultant biocompatible crosslinked polymer is controlled by the overall molecular weight of the crosslinker and functional polymer and the number of functional groups available per molecule. A lower molecular weight between crosslinks such as 600 will give much higher crosslinking density as compared to a higher molecular weight such as 10,000. Higher molecular weight functional polymers are preferred, preferably more than 3000 so as to obtain elastic gels.

The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density.

Preparation of Biodegradable Polymers

The biodegradable crosslinkers described in FIGS. 1 and 3 may be reacted with proteins, such as albumin, other serum proteins, or serum concentrates to generate crosslinked polymeric networks. Briefly, aqueous solutions of the crosslinkers described in FIG. 1 and FIG. 3 (at a concentration of 50 to 300 mg/ml) are mixed with concentrated solutions of albumin (600 mg/ml) to produce a crosslinked hydrogel. This reaction can be accelerated if a buffering agent, e.g., borate buffer or triethanol amine, is added during the crosslinking step.

The resultant crosslinked hydrogel is a semisynthetic hydrogel whose degradation depends on the degradable segment in the crosslinker as well as degradation of albumin by enzymes. In the absence of any degradable enzymes, the crosslinked polymer will degrade solely by the hydrolysis of the biodegradable segment. If polyglycolate is used as the biodegradable segment, the crosslinked polymer will degrade in 1-30 days depending on the crosslinking density of the network. Similarly, a polycaprolactone based crosslinked network will degrade in 1-8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to months, using a proper degradable segment.

The hydrophobicity generated by biodegradable blocks such as oligohydroxy acid blocks or the hydrophobicity of PPO blocks in Pluronic or Tetronic polymers are helpful in dissolving small organic drug molecules. Other properties which will be affected by incorporation of biodegradable or hydrophobic blocks are: water absorption, mechanical properties and thermosensitivity.

Totally synthetic gels can be produced when both the crosslinker and the functional polymer are synthetic in nature. For example, this could be done using as a crosslinker 4 arm PEG of molecular weight 10,000 daltons, extended with carboxymethyl ester of propanoic acid and terminated with NHS end groups. This crosslinker can be reacted with an 8 arm PEG amine functional polymer at a reaction pH of 9.5, and a solids concentration of 10%, with balanced stoichimetries for electrophilic and nucleophilic functionalities, to create a crosslinked biodegradable hydrogel within 5 seconds.

Synthetic gels can also be produced by using a small molecule as a crosslinker. For example, one could use a trilysine small molecular weight crosslinker and react it with a functional polymer such as 4 arm PEG of molecular weight 20,000 daltons, that is extended with Succinimidyl glutarate ester linkages and terminated with NHS end groups. At a reaction pH of 9.5 and a hydrogel solids concentration of 10%, with balanced stoichiometries for electrophilic and nucleophilic functionalities, a hydrogel can be formed within 5 seconds.

Methods of Using Biocompatible Polymers

The biocompatible crosslinked polymers and their precursors described above may be used in a variety of applications, such as components of tissue adhesives, tissue sealants, drug delivery vehicles, wound covering agents, barriers in preventing postoperative adhesions, and others. These and other suitable applications are reviewed in Schlag and Redl, "Fibrin Sealant" in *Operative Surgery*, volumes 1-7 (1986), which is incorporated herein by reference.

In Situ Formation

In many applications, the biocompatible crosslinked polymers of this invention typically will be formed "in situ" at a surgical site in the body. The various methodologies and devices for performing "in situ" gelation, developed for other adhesive or sealant systems such fibrin glue or sealant applications, may be used with the biocompatible crosslinked polymers of this invention. Thus, in one embodiment, an aqueous solution of a freshly prepared crosslinker (e.g. trilysine in a borate buffer solution at pH 9.5) and a functional polymer (e.g. 4 arm PEG of molecular weight 20,000 daltons, extended with Succinimidyl glutarate ester linkages and terminated with NHS end groups) are co-sprayed on to tissue using an air assisted sprayer such that the two fluid streams mix in the air and at the site of application to form a crosslinked biodegradable hydrogel that is capable of adhering to tissue within seconds. The two solutions may be applied simultaneously or sequentially. In some embodiments, it is preferred to apply the precursor solutions sequentially so as to "prime" the tissue, resulting in improved adherence of the biocompatible crosslinked polymer to the tissue. Where the tissue is primed, the crosslinker precursor is preferably applied to the tissue first, followed by the functional polymer solution.

One may use specialized devices to apply the precursor solutions, such as those described in U.S. Pat. Nos. 4,874,368; 4,631,055; 4,735,616; 4,359,049; 4,978,336; 5,116,315; 4,902,281; 4,932,942; Published PCT Patent Application No. WO 91/09641; and R. A. Tange, "Fibrin Sealant" in *Operative Medicine: Otolaryngology*, volume 1 (1986), the disclosures of which are herein incorporated by reference.

Drug Delivery

The subject crosslinkers, functional polymer and their reaction products, the crosslinked materials advantageously may be used for localized drug therapy. Biologically active agents or drug compounds that may be added and delivered from the crosslinked polymer or gel include: proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides.

To prepare such crosslinked composition, the bioactive compounds described above are mixed with the crosslinkable polymer prior to making the aqueous solution or during the aseptic manufacturing of the functional polymer. This mixture then is mixed with the crosslinker to produce a crosslinked material in which the biologically active substance is entrapped. Functional polymers made from inert polymers like Pluronic, Tetronics or Tween surfactants are preferred in releasing small molecule hydrophobic drugs.

In a preferred embodiment, the active agent or agents are present in a separate phase when crosslinker and crosslinkable polymers are reacted to produce a crosslinked polymer network or gel. This phase separation prevents participation of bioactive substance in the chemical crosslinking reaction such as reaction between NHS ester and amine group. The separate phase also helps to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly(lactone)s and poly(hydroxy acid) are particularly preferred as biodegradable encapsulation vehicles.

In using crosslinked materials which are described herein as drug delivery vehicles, the active agent or encapsulated active agent may be present in solution or suspended form in crosslinker component or functional polymer solution component. The nucleophilic component, whether it be in the crosslinker or the functional polymer is the preferred vehicle due to absence of reactive groups. The functional polymer along with bioactive agent, with or without encapsulating vehicle, is administered to the host along with equivalent amount of crosslinker and aqueous buffers. The chemical reaction between crosslinker and the functional polymer solution readily takes place to form a crosslinked gel and acts as a depot for release of the active agent to the host. Such methods of drug delivery find use in both systemic and local administration of an active agent.

In using the crosslinked composition for drug delivery as mentioned above, the amount of crosslinkable polymer, crosslinker and the dosage agent introduced in the host will necessarily depend upon the particular drug and the condition to be treated. Administration may be by any convenient means such as syringe, canula, trocar, catheter and the like.

Several methods for the formation of regional adhesion barriers are described, in which any of a variety of water soluble macromeric precursors are used. The term "macromeric precursor" or "macromer" is meant to connote an oligomeric or polymeric molecule that contains functional groups that enable further crosslinking. Preferably the functionality of a macromer molecule is >2 so that a crosslinked network or hydrogel results upon crosslinking.

In one embodiment, a crosslinked regional barrier is formed in situ, for example, by electrophilic-nucleophilic reaction, free radical polymerization initiated by a redox system or thermal initiation, wherein two components of an initiating system are simultaneously, sequentially or separately instilled in a body cavity to obtain widespread dispersal and coating of all or most visceral organs within that cavity prior to gelation and crosslinking of the regional barrier. Once the barrier is formed, the organs remain isolated from each other for a predetermined period, depending upon the absorption profile of the adhesion barrier material.

Preferably, the barrier is selected to have a low stress at break in tension or torsion, so as to not adversely affect normal physiological function of visceral organs within the region of application. The barrier also may contain a drug or other therapeutic agent.

Certain embodiments of the invention are accomplished by providing compositions and methods to control the release of relatively low molecular weight therapeutic species using hydrogels. In accordance with the principles of the present invention, a therapeutic species first is dispersed or dissolved within one or more relatively hydrophobic rate modifying agents to form a mixture. The mixture may be formed into microparticles, which are then entrapped within a bioabsorbable hydrogel matrix so as to release the water soluble therapeutic agents in a controlled fashion. Alternatively, the microparticles may be formed in situ during crosslinking of the hydrogel.

In one method of the present invention, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water soluble therapeutic agent may be dispersed in the polymerizable phase, or formed in situ, to form an emulsion. Polymerization and crosslinking of the emulsion and the immiscible phase is initiated in a controlled fashion after dispersal of the polymerizable phase into appropriately sized microspheres, thus entrapping the microparticles in the hydrogel microspheres. Visualization agents may be included, for instance, in the microspheres, microparticles, and/or microdroplets.

Embodiments of the invention include compositions and methods for forming composite hydrogel-based matrices and microspheres having entrapped therapeutic compounds. In one embodiment, a bioactive agent is entrapped in microparticles having a hydrophobic nature (herein called "hydrophobic microdomains"), to retard leakage of the entrapped agent. More preferably, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent.

Hydrophobic microdomains, by themselves, may be degraded or quickly cleared when administered in vivo, making it difficult to achieve prolonged release directly using microdroplets or microparticles containing the entrapped agent in vivo. In accordance with the present invention, however, the hydrophobic microdomains are sequestered in a gel matrix. The gel matrix protects the hydrophobic microdomains from rapid clearance, but does not impair the ability of the microdroplets or microparticles to release their contents slowly. Visualization agents may be included, for instance, in the gel matrix or the microdomains.

In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in commonly assigned U.S. patent application Ser. No. 09/134,287 entitled "Composite Hydrogel Drug Delivery Systems"; Ser. No. 09/390,046 entitled "Methods and Apparatus for Intraluminal Deposition of Hydrogels"; and Ser. No. 09/134,748 entitled "Methods for Forming Regional Tissue Adherent Barriers and Drug Delivery Systems", each of which are hereby incorporated by reference.

In another aspect of the present invention, the hydrogel microspheres are formed having a size that will provide selective deposition of the microspheres, or may linked with ligands that target specific regions or otherwise affect deposition of the microspheres within a patient's body.

Controlled rates of drug delivery also may be obtained with the system of the present invention by degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

Composite Biomaterials

The biocompatible crosslinked polymers of this invention optionally may be reinforced with flexible or rigid fibers, fiber mesh, fiber cloth and the like. The insertion of fibers improves mechanical properties like flexibility, strength, and tear resistance. In implantable medical applications, biodegradable fibers, cloth, or sheets made from oxidized cellulose or poly(hydroxy acid)s polymers like polylactic acid or polyglycolic acid, are preferred. Such reinforced structures may be produced using any convenient protocol known in the art.

In a preferred method, aqueous solutions of functional polymers and crosslinkers are mixed in appropriate buffers and proportions are added to a fiber cloth or net such as Interceed (Ethicon Inc., New Brunswick, N.J.). The liquid mixture flows into the interstices of the cloth and becomes crosslinked to produce a composite hydrogel. Care is taken to ensure that the fibers or fiber mesh are buried completely inside the crosslinked hydrogel material. The composite structure can be washed to remove side products such as N-hydroxysuccinimide. The fibers used are preferably hydrophilic in nature to ensure complete wetting of the fibers by the aqueous gelling composition.

EXAMPLES

The following non-limiting examples are intended to illustrate the synthesis of new biocompatible crosslinked polymers and their precursors, and their use in making several medical products. Those skilled in the art will appreciate that modifications can be made to these examples, drawings, illustrations and claims that are intended to fall within the scope of the present invention.

Materials and Equipment

Polyethylene glycol was purchased from various sources such as Shearwater Polymers, Union Carbide, Fluka and Polysciences. Multifunctional hydroxyl and amine terminated polyethylene glycol were purchased from Shearwater Polymers, Dow Chemicals and Texaco. Pluronic® and Tetronic® series polyols were purchased from BASF Corporation. DL-lactide, glycolide, caprolactone and trimethylene carbonate was obtained from commercial sources like Purac, DuPont, Polysciences, Aldrich, Fluka, Medisorb, Wako and Boehringer Ingelheim. N-hydroxysulfosuccinimide was purchased from Pierce. All other reagents, solvents were of reagent grade and were purchased from commercial sources such as Polysciences, Fluka, Aldrich and Sigma. Most of the reagents and solvents were purified and dried using standard laboratory procedures such as described in D. D. Perrin et al., Purification of Laboratory Chemicals (Pergamon Press 1980). Compounds that contain PEG, including multi-armed electrophiles and nucleophiles, are available by catalog or custom order from Shearwater Polymers Inc. (Huntsville, Ala.), NOF corporation, especially in the NOF "SUNBRIGHT SERIES" (Tokyo, Japan), SUNBIO (Seoul, Korea), and Polymer Source, Inc. (Montreal, Canada).

General Analysis

The polymers synthesized according to these examples were chemically analyzed using structure-determining methods such as nuclear (proton and carbon-13) magnetic resonance spectroscopy, infrared spectroscopy. Molecular weights were determined using high pressure liquid chromatography and gel permeation chromatography. Thermal characterization of the polymers, including melting point and glass transition temperatures, were performed using differential scanning calorimetric analysis. Aqueous solution properties such as micelle and gel formation was determined using fluorescence spectroscopy, UV-visible spectroscopy and laser light scattering instruments.

In vitro degradation of the polymers was followed gravimetrically at 37° C., in an aqueous buffered medium such as phosphate buffered saline (at pH 7.2). In vivo biocompatibility and degradation life times was assessed by injecting or forming a gelling formulation directly into the peritoneal cavity of a rat or rabbit and observing its degradation over a period of 2 days to 12 months.

Alternatively, the degradation was also assessed by prefabricating a sterile implant, made by a process like solution casting, then surgically implanting the implant within an animal body. The degradation of the implant over time was monitored gravimetrically or by chemical analysis. The biocompatibility of the implant was assessed by standard histological techniques.

Example 1

Synthesis of a Water-soluble Difunctional, Biodegradable Functional Polymer Based on Polyalkylene Oxide Block Copolymer First, Polyethylene glycol-co-polycaprolactone polyol ("F68C2") was synthesized as follows:

30 g of Pluronic F68 was dried under vacuum at 110° C. for 6 h and then mixed with 1.710 g of caprolactone and 30 mg of stannous 2-ethylhexanoate in a glass sealing tube. The glass tube then was sealed under nitrogen atmosphere and heated to 170° C. and maintained at this temperature for 16 h. The Pluronic F68-caprolactone polymer was cooled and recovered by breaking the glass sealing tube, and then further purified by several precipitations from a toluene-hexane solvent-nonsolvent system.

The polymer then was dried in vacuum at 40° C. and used immediately in the activation reaction described below:

Reaction with succinic anhydride ("11F68C2S"):

30 g of Pluronic F68-caprolactone copolymer was dissolved in 200 ml dry N,N-dimethyl formamide ("DMF") and 0.845 g of succinic anhydride was added to the reaction mixture. The mixture was heated to 100° C. under a nitrogen atmosphere for 16 h. The solution then was cooled and added to 4000 ml hexane to precipitate the carboxyl terminated polymer. It was further purified by repeated (3 times) precipitation from a toluene-hexane solvent-nonsolvent system. The polymer was dried under vacuum at 40° C.

This polymer was immediately used in activation reaction described below:

Activation of Carboxyl Groups with N-hydroxysuccinimide ("F68C2SSNHS"):

30 g of Pluronic F68-caprolactone succinate copolymer was dissolved in 200 ml dry DMF. The solution was cooled to 4° C. and 1.504 g of 1,3-dicyclohexylcarbodiimide ("DCC") and 1.583 g of N-hydroxysulfosuccinimide ("SNHS") were added to the reaction mixture. The mixture was stirred at 4° C. for 6 h and then stirred overnight at room temperature under nitrogen atmosphere. Dicyclohexylurea was removed by filtration and the F68C2S-SNHS derivative was isolated by removing the DMF under vacuum and repeated precipitation using a toluene-hexane solvent-nonsolvent system. The product was stored under nitrogen atmosphere at −20° C.

Example 2

Amine Terminated Synthetic Biodegradable Crosslinkable Polymer

Reaction of F68TMC2SSNHS with Lysine.

3.55 g of lysine was dissolved in 200 ml 0.1M borate buffer (pH 8.5). The mixture was cooled to 0° C. in ice bath and 10 g of F68C2SSNHS were added to the mixture. The mixture was stirred for 6 h at room temperature and lyophilized. The lyophilized powder was dissolved in 30 ml toluene and filtered. The filtrate was added to 4000 ml cold diethyl ether. The precipitated amine terminated polymer was recovered by filtration and dried under vacuum. The polymer was stored under argon at −20° C.

Example 3

Synthesis of Carboxyl Terminated Oligolactic Acid Polymer Activated with N-hydroxysulfosuccinimide Synthesis of difunctional oligolactate with terminal carboxyl acid end-groups activated with N-hydroxysulfosuccinimide groups.

Part 1: Synthesis of Oligomeric poly(lactic acid) with Terminal Carboxyl Acid Groups ("PLA-S").

In a 250 ml 3 neck flask equipped with mechanical stirrer, nitrogen inlet and distillation condenser, 2 grams of succinic acid and 34.1 ml 1N HC 1 and 3.83 g L-lactic acid, sodium salt were charged. The flask was then immersed in a silicone oil bath maintained at 150° C. Most of the water from the reaction mixture was removed over period of 5 hours by distillation. The remaining water was removed by heating the reaction mixture under vacuum at 180° C. for 15 h. The reaction mixture was cooled and lyophilized at 0° C. to remove traces of water. The product was isolated by dissolving in toluene and precipitating in hexane. The precipitated polymer was isolated by filtration and dried in vacuum for 48 h at 60° C.

Part 2: Activation of Terminal Groups with N-hydroxysulfosuccinimide Group:

A 3 necked flask equipped with magnetic stirrer and nitrogen inlet was charged with 2 g of PLA-S copolymer and 20 ml DMF. The solution was cooled 4° C. and 3.657 g of N-hydroxysulfosuccinimide and 3.657 g of 1,3-dicyclohexyl carbodiimide were added to the reaction mixture. The mixture was stirred at 4° C. for 6 h and overnight at room temperature under nitrogen atmosphere. Dicyclohexylurea was removed by filtration and SNHS derivative was by isolated by removing the DMF under vacuum and repeated precipitation using toluene-hexane solvent-nonsolvent system. The product was stored under nitrogen atmosphere at 4° C.

Example 4

Preparation of Polyethylene Glycol Based Tetrafunctional Crosslinker

Part 1: Synthesis of Tetrafunctional Polyethylene glycol-co-polyglycolate Copolymer ("4PEG2KG"):

30 grams of 4 arm polyethylene glycol, molecular weight 2000 ("4PEG2K") was dried at 100° C. for 16 hours prior to use. 30 grams 4PEG2K. 7.66 g of glycolide and 25 mg of stannous 2-ethylhexanoate were charged into a 3 necked flask equipped with a Teflon coated magnetic stirring needle. The flask was then immersed into silicone oil bath maintained at 160° C. The polymerization reaction was carried out for 16 h under nitrogen atmosphere. At the end of the reaction, the reaction mixture was dissolved in 100 ml toluene. The hydroxy terminated glycolate copolymer was isolated by pouring the toluene solution in 4000 ml cold hexane. It was further purified by repeated dissolution-precipitation process from toluene-hexane solvent-nonsolvent system and dried under vacuum at 60° C. It then was immediately used for end capping reaction mentioned below:

Part 2: Conversion of Hydroxyl Groups into Carboxylic Groups ("4PEG2KGS") and SNHS Ester.

30 g of 4PEG2KG copolymer was dissolved in 150 ml dry pyridine. 8.72 g of succinic anhydride was added to it and the solution was refluxed for 2 h under nitrogen atmosphere. The polymer was isolated by pouring the cold pyridine solution to 4000 ml hexane. The acid terminated polymer ("4PEG2KGS") was used in SNHS activation reaction. Briefly, to a solution of 30 g of 4PEG2KGS in 300 ml dry methylene chloride were added 10.58 g of SNHS and 10.05 g DCC. The reaction mixture was stirred overnight under nitrogen atmosphere. Dicyclohexylurea was removed by filtration. The filtrate was evaporated and the residue obtained was redissolved in 100 ml toluene. The toluene solution was precipitated in 2000 ml hexane. The SNHS activated polymer was stored under nitrogen atmosphere until further use.

Example 5

Sulfonyl Chloride Activated Crosslinkers

Activation of tetrafunctional polyethylene glycol-co-polyglycolate copolymer ("4PEG2KGS") with tresyl chloride.

30 g of 4PEG2KG was dissolved in 10 ml dry benzene. The solution was cooled to 0° C. and 5.92 g of triethyl amine and 10.70 g tresyl chloride were added under nitrogen atmosphere. After refluxing for 3 h under nitrogen atmosphere, the reaction mixture was cooled and filtered to remove triethylamine hydrochloride. The filtrate was poured into 3000 ml hexane to precipitate the activated polymer. The residue was redissolved in THF and filtered over neutral alumina to remove traces of triethylamine hydrochloride. The polymer was recovered by adding the THF solution to 3000 ml diethyl ether and stored under nitrogen atmosphere.

Example 6

Synthesis of Multifunctional Oligopolycaprolactone Terminated with SNHS

Part 1: Synthesis of Polycaprolactone ("PCL1").

2.00 g of glycerol, 8.17 g of caprolactone and 50 mg of stannous 2-ethylhexanoate were charged into 100 ml Pyrex pressure sealing tube. The tube was frozen in liquid nitrogen and connected to vacuum line for 10 minutes. The tube then was connected to argon gas line and sealed under argon. The sealed reaction mixture then was immersed in oil bath maintained at 160° C. and polymerization was carried out for 16 h at 160° C. The polymer was recovered by dissolving it in 30 ml toluene and precipitating in 2000 ml cold hexane. The precipitated liquid oligomer was recovered and dried under vacuum for 1 day at 60° C.

Part 2: End-capping of PCL1 with Succinic Anhydride ("PCL-S"):

10 g of PCL1 was dissolved in 150 ml dry benzene. About 50 ml of benzene was distilled to remove traces of water from the reaction mixture. The solution was cooled to 30° C. To this warm solution, 6.67 g of triethyl amine and 7.86 g of succinic anhydride were added. The reaction mixture was then refluxed for 6 h and concentrated by distillation under vacuum. The product was recovered by adding the filtrate to 2000 ml cold dry hexane.

Part 3: Activation of PCL-S with SNHS:

PCL1-succinate (5.0 g) was dissolved in 10 ml of anhydrous methylene chloride, cooled to 0° C. and 7.82 g of N-hydroxysulfosuccinimide and 7.42 N,N-dicyclohexylcarbodiimide were added under stirring. After stirring the mixture overnight, the precipitated dicyclohexylurea was removed by filtration and the solution was concentrated by removing solvent. The $H^1$-NMR spectrum showed succinimide singlet at 2.80 ppm (2H).

Example 7

Preparation of Polyethylene glycol-co-polytrimethylene Carbonate Copolymer Terminated with N-hydroxysuccinimide Preparation of tetrafunctional polyethylene glycol-co-polytrimethylene carbonate copolymer ("4PEG10KTMC2").

30 g of tetrahydroxy polyethylene glycol, molecular weight 10000, was dried under vacuum at 90-100° C. in a glass sealing tube. The tube then was cooled and transferred inside an air bag where 2.45 g of trimethylene carbonate and 20 mg of stannous octoate were added to the tube. The glass tube was then sealed under vacuum and heated with stirring at 155° C. and maintained at this temperature for 16 h. The polyethylene glycol-co-polytrimethylene carbonate polymer was cooled and recovered by breaking the glass sealing tube. It was further purified by several precipitations from toluene-hexane solvent-nonsolvent system.

Part 2: Synthesis of Glutarate Derivative of 4PEG10KTMC2 ("4PEG10KTMC2G"):

10 g of 4PEG10KTMC was dissolved in 120 ml dry toluene. About 50 ml of toluene was distilled to remove traces of water from the reaction mixture. The warm solution was cooled to 60° C. To this solution, 1.23 g of triethyl amine and 1.40 g of glutaric anhydride were added. The reaction mixture was heated to 60° C. for 1 h and filtered. The product was recovered by adding the filtrate to 2000 ml cold dry hexane.

Part 3: Activation of Terminal Carboxyl Groups Using N-hydroxysuccinimide ("4PEG10KTMC2GNHS"):

30 g of 4PEG10KTMC2G was dissolved in 100 ml of dry DMF and 1.53 g of N-hydroxysuccinimide and 5 g molecular sieves 3 Å were added. 1.28 g of DCC dissolved in 5 ml dry DMF was added dropwise and the reaction mixture was kept at room temperature for 24 h under nitrogen atmosphere. The mixture was diluted with 50 ml cold benzene and precipitated using cold hexane. The precipitate was collected on a sintered glass filter with suction. The dissolution and precipitation procedure was then repeated three times, using toluene-diethyl ether as solvent-nonsolvent system and dried under vacuum. The product was stored under nitrogen atmosphere at −20° C. until further use.

Example 8

Succinated Polyhydroxy Compounds Activated with N-hydroxysulfosuccinimide ES 10 g of erythritol was dissolved in 200 ml dry toluene. About 50 ml of toluene was distilled to remove traces of water from the erythritol. The solution was cooled to 50-60° C. and 20 ml pyridine and 8.58 g of succinic anhydride were added to the solution. The reaction mixture was then refluxed for 3 h and unreacted pyridine and toluene were evaporated to dryness under reduced pressure. The residue was used in activation reaction.

Part 2: Activation of ES with SNHS:

Erythritol-succinate (ES, 2.0 g) was dissolved in 10 ml of anhydrous dimethyl formamide ("DMF"), cooled to 0° C. and 3.47 g of N-hydroxysulfosuccinimide and 3.30 N,N-dicyclohexylcarbodiimide were added under stirring. After stirring the mixture overnight, the precipitated dicyclohexylurea was removed by filtration and the solution was concentrated by removing solvent. It was further purified by column chromatography.

Example 9

Preparation of Synthetic Crosslinked Biodegradable Gels 1.57 g (0.8 mM) of 4 arm amine terminated polyethylene glycol molecular weight 2000 was dissolved in 10 ml 0.1 M sodium borate buffer at pH 9.5 2 g of 4 arm SNHS activated 4PEG2KGS polymer (molecular weight 2500) was dissolved in phosphate buffered saline. These two solutions were mixed to produce a crosslinked gel. In another variation of this method, the 4PEG2KGS polymer solid was directly added to the amine terminated polymer solution to produce a crosslinked polymer.

In another variation, a crosslinker consisting of an equimolar solution of dilysine can be used in place of the 4 arm PEG amine solution to form a hydrogel. Gelation was seen to occur within 10 seconds of mixing the two solutions. Similarly, other crosslinkers described in examples 1 to 7 may be reacted in molar equivalent proportions with other amine terminated polymers such as albumin or amine terminated biodegradable polymers similar to described in Example 2. The preferred compositions for making biodegradable hydrogels were described in Table 2. The amine terminated polymer solution described above was added with 0.1% of F D and C blue or indigo dye prior to crosslinking reaction. The addition of dye allows the preparation of colored gels.

Example 10

Preparation of Composite Synthetic Crosslinked Colored Biodegradable Gels 3 grams of bovine serum albumin was dissolved in 3 ml of phosphate buffered solution. Commercial sutures based on synthetic biodegradable polymers, such as Vicryl was cut/ground into several small pieces (size less than 1 mm) using cryogenic grinding. These colored suture particles (approximately 100 mg) were mixed with the albumin solution to form a suspension. 100 mg of crosslinker such as 4PEG10KTMC2GNHS was mixed with 0.2 ml of albumin suspension. This viscous solution then was mixed with 40 mg of triethanol amine (buffering agent). The addition of triethanol amine gels the solution in 60 seconds. The colored suture particles entrapped in the crosslinked gel help to visualize the gel especially when under laparoscopic conditions and also acts to strengthen the hydrogel as a reinforcing agent. The suture particles in above examples can be replaced with biodegradable microparticles loaded with drugs or bioactive compounds.

Example 11

Formulation of SG-PEG with Di-lysine

A four arm PEG with SG end groups (Shearwater Polymers, approx. 9,100 g/mol, 0.704 grams, $6.5 \times 10^{-5}$ moles) was dissolved in 2.96 g 0.01M pH 4.0 phosphate buffer (19.2% solids). Di-lysine (Sigma, 347.3 g/mol, 0.03 grams, $8.7 \times 10^{-5}$ moles) was dissolved in 3.64 grams of 0.1M pH 9.5 borate buffer (0.8% solids). On combination of the two solutions, the percent solids was 10%. The di-lysine has 3 amine groups. The SG-PEG has 4 NHS groups. After correction for the less than 100% degree of substitution on the SG-PEG, the formulation gives a 1:1 stoichiometry of amine groups to NHS groups.

Example 12

Formulation of SG-PEG with Tri-lysine

A four arm PEG with SG end groups (Shearwater Polymers, approx. 9,100 g/mol, 0.675 grams, $6.2 \times 10^{-5}$ moles) was dissolved in 2.82 g 0.01M pH 4.0 phosphate buffer (19.3% solids). Tri-lysine (Sigma, 402.5 g/mol, 0.025 grams, $6.2 \times 10^{-5}$ moles) was dissolved in 3.47 grams of 0.1M pH 9.5 borate buffer (0.7% solids). On combination of the two solutions, the percent solids was 10%. The tri-lysine has 4 amine groups. The SG-PEG has 4 NHS groups. After correction for the less than 100% degree of substitution on the SG-PEG, the formulation gives a 1:1 stoichiometry of amine groups to NHS groups.

Example 13

Formulation of SG-PEG with Tetra-lysine

A four arm PEG with SG end groups (Shearwater Polymers, approx. 9,100 g/mol, 0.640 grams, $5.9 \times 10^{-5}$ moles) was dissolved in 2.68 g 0.01M pH 4.0 phosphate buffer (19.2% solids). Tetra-lysine (Sigma, 530.7 g/mol, 0.025 grams, $4.7 \times 10^{-5}$ moles) was dissolved in 3.30 grams of 0.1M pH 9.5 borate buffer (0.8% solids). On combination of the two solutions, the percent solids was 10%. The tetra-lysine has 5 amine groups. The SG-PEG has 4 NHS groups. After correction for the less than 100% degree of substitution on the SG-PEG, the formulation gives a 1:1 stoichiometry of amine groups to NHS groups.

Example 14

Gel Time Measurement

Figure 11:
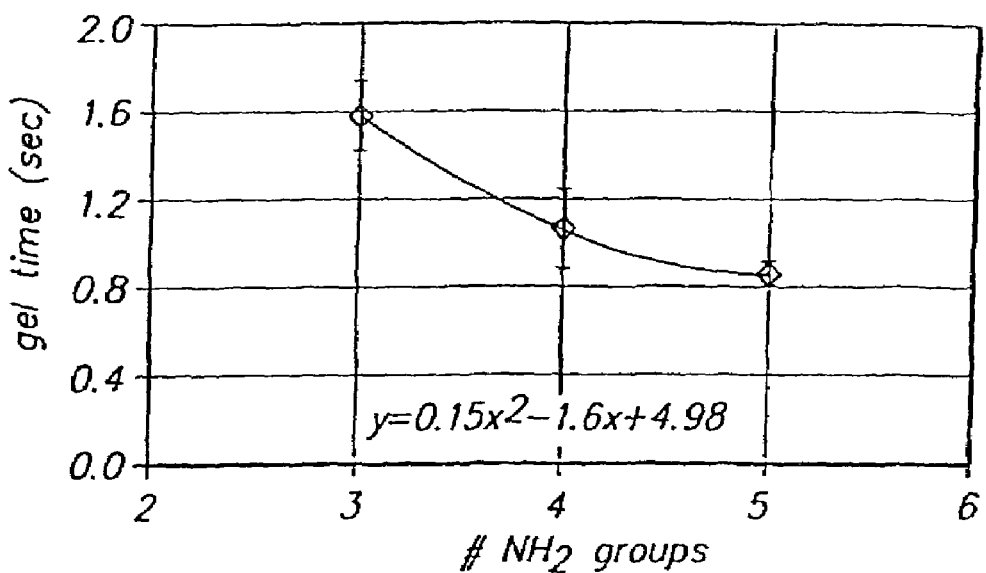
FIG. 11 shows the variation in gelation time with the number of amino groups for the reaction of 4 arm 10 kDa succinimidyl glutarate PEG ("SG-PEG") with di-, tri- or tetra-lysine.

The amine solution (100 μL) was aliquotted into a 100×13 test tube. A flea-stir bar (7×2 mm, Fisher Scientific p/n 58948-976) was placed in the test tube. The test tube was held stationary over a digital magnetic stirrer (VWR Series 400S Stirrer) set at 300 rpm. A 1 cc tuberculin syringe (Becton Dickinson, p/n BD309602) was filled with 100 μL of the ester solution. The syringe was inserted up to the flanges so that the distal end was just over the amine solution. Simultaneously the plunger was depressed and a stop watch started. When the solution solidifies sufficiently so that the stir bar stops spinning, the stop watch was stopped. Each solution was measured in triplicate and the mean±1 standard deviation was plotted. Results for the formulations of Examples 11, 12 and 13 are shown in FIG. 11.

Example 15

Change in Gel Time as a Function of Ester Solution Age

Figure 12:
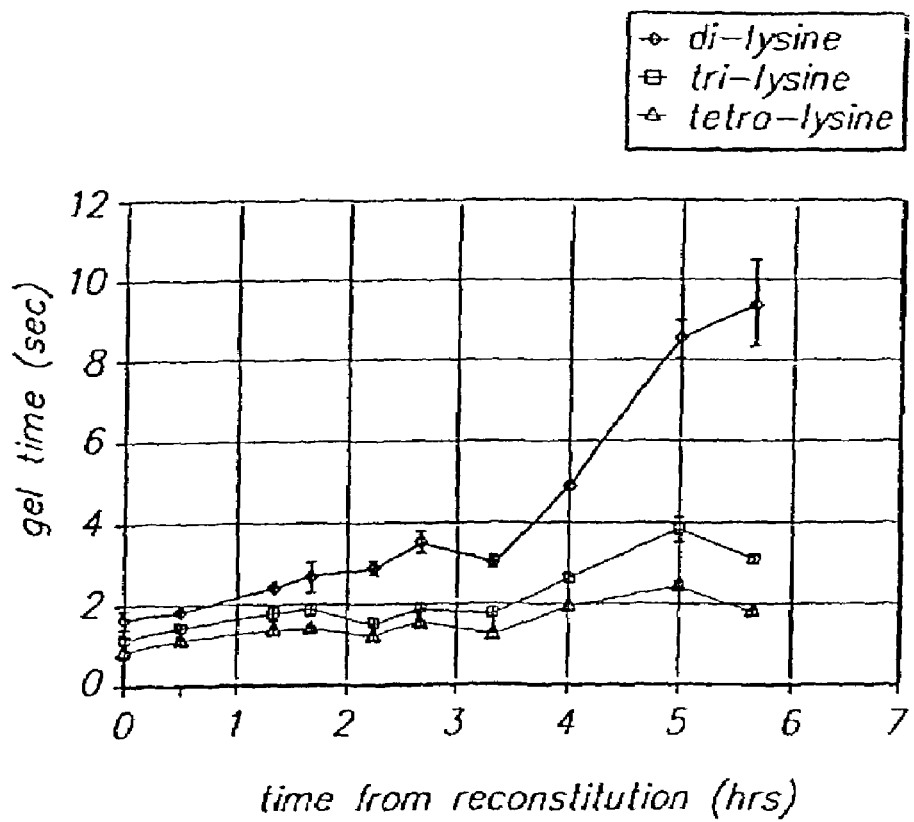
FIG. 12 shows gelation time for the compositions of FIG. 11 as a function of the solution age of the electrophilic functional polymer.

An important characteristic of these systems is the loss in reactivity over time from reconstitution of the ester solution. This loss in reactivity occurs due to hydrolysis of the N-hydroxysuccinimidyl ester, before the activated molecule can combine with its respective nucleophilic functional group. The loss of reactivity was characterized by measuring the change in gel time as a function of time from reconstitution of the NHS ester solution. The gel time was measured periodically. The NHS ester solution was stored at ambient conditions during this measurement. Results for the solutions described in Examples 11, 12 and 13 are shown in FIG. 12.

Example 16

Gel Formation at Different Percent Solids from 4 Arm CM-HBA-NS PEG and Lys-Lys Using the gel time method described in Example 13, five different gel compositions were made using carboxymethyl hydroxybutyrate-hydroxysuccinimide end-capped 4 arm PEG (CM-HBA) (Shearwater Polymers) and di-lysine (Sigma). The formulations are listed below in Table 3.

TABLE 3

| Conc. (%) | CM-HBA (g) | Phosphate (g) | Lys-Lys (g) | Borate (g) |
|---|---|---|---|---|
| 8.5 | 0.2469 | 1.264 | 0.01 | 1.5012 |
| 10 | 0.2904 | 1.2209 | 0.012 | 1.4994 |
| 12.5 | 0.363 | 1.1483 | 0.015 | 1.4964 |
| 15 | 0.4356 | 1.0757 | 0.018 | 1.4936 |
| 20 | 0.5808 | 0.9305 | 0.024 | 1.4876 |

Figure 13:
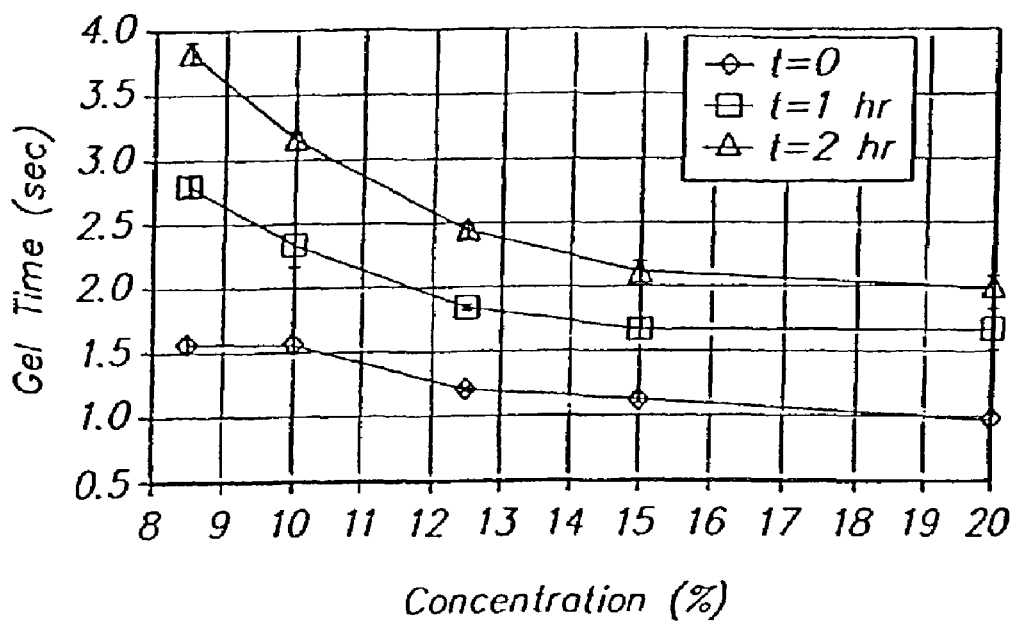
FIG. 13 shows the variation in gelation time with the concentration of biocompatible crosslinked polymer precursors, and with the solution age of the 4 arm 10 kDa carboxymethyl-hydroxybutyrate-N-hydroxysuccinimidyl PEG ("CM-HBA-NS") electrophilic functional polymer, as is further described in Example 16.

The formulations were adjusted to give a 1 to 1 ratio of electrophilic functional end groups on the CM-HBA (4) to nucleophilic reactive groups on the di-lysine ("Lys-Lys")(3). The CM-HBA quantities were dissolved in 0.01M pH 5.0 phosphate buffer. The di-lysine was dissolved in 0.1M pH 11 borate buffer. Gel time results are shown in FIG. 13. This data also shows that the higher percent solids solutions also are the most stable with respect to retention of speed of reaction.

Example 17

Degradation of Hydrogels

Figure 14:
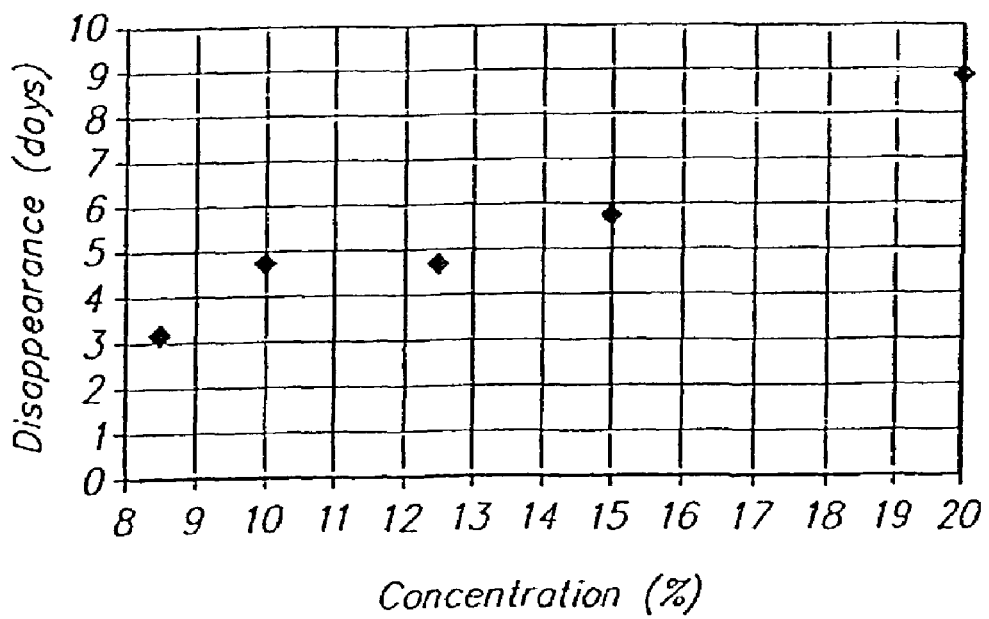
FIG. 14 shows the variation in degradation time with the concentration of biocompatible crosslinked polymer, as is further described in Example 17.

Hydrogel plugs made during the gel time measurements of Example 14 were placed in approximately 25 mL 0.1M phosphate buffered saline at pH 7.4 in 50 mL Falcon tubes and placed in a constant temperature bath at 37° C. The hydrogel plugs were observed visually at periodic intervals and the time of gel disappearance noted. The data are plotted in FIG. 14.

Example 18

Precursor Spray Procedure to Form a 7.5% Solids Hydrogel from 4 Arm SG and Dilysine An ethylene oxide sterilized air assisted sprayer was used in conjunction with aqueous solutions of polymerizable monomers. Solution 1 consisted of a 14.4% solution of 4 arm SG (MW 10,000 purchased from Shearwater Polymers) dissolved in 0.01M phosphate buffer at pH 4.0 and was sterile filtered (Pall Gelman syringe filter, p/n 4905) and drawn up in a sterile 5 cc syringe. Solution 2 consisted of a 1.2% solution of a dilysine (purchased from Sigma Chemicals) dissolved in 0.1M borate buffer at pH 11 with 0.5 mg/ml methylene blue for visualization and was also sterile filtered and drawn up in a sterile 5 cc syringe. These solutions, when combined 1:1 on a volumetric basis, resulted in a 1:1 ratio of NHS ester to amine end group. The final % solids after combination was 7.5%. The two syringes were individually loaded in the two separate receptacles through a luer-lok type of linkage. Airflow from a regulated source of compressed air (an air compressor such as those commercially available for airbrushes) was connected to the device using a piece of Tygon tube. On compressing the syringe plungers a steady spray of the two liquid components was observed. When this spray was directed to a piece of tissue (rat cecum) a hydrogel coating was observed to form on the surface of the tissue. This hydrogel coating was rinsed with saline (the hydrogel coating is resistant to rinsing) and was observed to be well adherent to the tissue surface. Within a short period of time (less than a minute) an area of 10 cm×5 cm could be coated with ease.

Example 19

Precursor Spray Procedure to Form a 12.5% Solids Hydrogel from 4 Arm CM and Dilysine A hydrogel barrier film made from 4 arm CM-HBA NS (MW 10,000 purchased from Shearwater Polymers), and dilysine was similarly prepared and sprayed as described in Example 18. In the present example the 4 arm CM solution was made up to 24.0% solids and the dilysine solution was made up to 1.0% solids such that on combination in an equal volume delivery system a 1:1 ratio of NHS to amine end groups results, giving a final % solids of 12.5%.

Example 20

Spray Application of Crosslinker and Polymer to from Crosslinked Film

Two solutions (component A and component B) were prepared. Component A consisted of dilysine in 0.1M borate buffer, pH 9.5. Component B consisted of either 4 arm SG-PEG or 4 arm CM-HBA-NS in 0.01M phosphate buffer, pH 4.0 These solutions were prepared such that the amine to ester stoichiometric ratio was 1:1 and the final total solution concentration was 7.5% or 12.5%, respectively.

A Fibriject™ (Micromedics, Inc.) 5 cc syringe holder and cap was used, preloaded with 5 cc of each solution and attached to a dual barrel atomizing sprayer. The sprayer has two hubs for the syringes to connect to allowing the two fluids to be advanced through two separate lumens over any preset distance. A third hub exists for the application of the atomizing gas. Air was used in this example. The distal tip of the sprayer contains a chamber where the gas expands out of an introduction tube, then flows past the two polymer solution nozzles in an annular space around each. The gas is accelerated in the annular spaces using a flow rate suitable for the complete atomization of the two fluid streams (~2 L/min.). Two overlapping spray cones are thus formed allowing for well mixed, thin, uniform coatings to be applied to surfaces.

Example 21

Adhesion Prevention in Rat Cecum Model

Surgical Procedure

Male Sprague Dawley rats (250-300 grams,) were anesthetized with an intramuscular 4 ml/kg "cocktail" of Ketamine (25 mg/ml), Xylazine (1.3 mg/ml) and Acepromazine (0.33 mg/ml). The abdominal area was shaved and prepped for aseptic surgery. A midline incision was made to expose the abdominal contents. The cecum was identified and location within the abdomen was noted. The cecum was pulled out of the abdomen and the surface of one side was abraded using dry sterile gauze. A technique of abrading one area by stroking the surface 12 times with the gauze was used. The cecal arterial supply was interrupted using bipolar coagulation along the entire surface area of the damaged cecum.

The opposing abdominal sidewall which lays in proximity to the damaged cecal surface was deperitonealized with a scalpel blade and the underlying muscle layer was scraped to the point of hemorrhaging.

The cecum was sprayed with either the SG-PEG system or the CM-HBA-NS system using the air assisted spray method described in the preceding example. The cecum was placed with the damaged (ischemic area) side up opposite the damaged side wall. Active bleeding was controlled before closing. The peritoneum and muscle wall was closed with 3-0 nylon and the skin was closed with 4-0 silk. Rats were returned to their cages for one to two weeks at which time evaluation of the adhesion between the side wall and cecum was noted. The rats were killed at 10 days and the tenacity and extent of adhesion was evaluated. The results are summarized in Table 4.

TABLE 4

| Rat # | Material Applied | Reference Example | Finding on Day 10 |
|---|---|---|---|
| 403 | 7.5% 4aSG with Lys-Lys w/MB | Example 18 | Small amount of gel present on cecum. No adhesions from cecum to sidewall. No gel on sidewall |
| 404 | 7.5% 4aSG with Lys-Lys w/MB | Example 18 | Some mesentery stuck to cecum. No gel. No adhesions. |
| 405 | 7.5% 4aSG with Lys-Lys w/MB | Example 18 | Small amount of gel present on cecum. Some mesentery stuck to cecum and sidewall. Some gel between mesentery and cecum where stuck. No adhesions. |
| 406 | 12.5% 4aCM with Lys-Lys w/MB | Example 19 | No gel present. No adhesions. |
| 407 | 12.5% 4aCM with Lys-Lys w/MB | Example 19 | No gel on cecum or sidewall. No adhesions. |
| 408 | 12.5% 4aCM with Lys-Lys w/MB | Example 19 | Rat died post-op (anesthesia overdose). |

Example 22

MIS Application of Hydrogels with Coloring Agent

This example is directed to concentrations of coloring agent for use in an in situ crosslinked hydrogel coating. A 140 mg amount of four-arm primary amine terminated polyethylene glycol molecule with a molecular weight of approximately 10,000 was dissolved in sodium borate buffer pH 9.5. An 84 mg amount of four arm NHS activated polyethylene glycol polymer (SPA-3400, Shearwater Corp., Huntsville, Ala., molecular weight approximately 3400) was dissolved in pH 5.0 acetate buffer. Methylene Blue was added to the borate buffered solutions at concentrations of 0.1, 0.5, and 1.0 mg/ml.

A standard laparoscopic sprayer was used in a laparoscopic trainer to spray the surfaces of pieces of lunch meat with an approximately 1:1 mixture of the solutions. The mixture formed a gel in about 3-6 seconds on the surfaces. The sprayed gel was observed through a 10 mm laparoscope and videotaped. The tapes were reviewed to assess the effect of the coloring agent. The 0.5 mg/ml and 1.0 mg/ml solutions of coloring agent created a gel that was readily observable and similar in visibility. The 0.1 mg/ml solution of coloring agent created a gel that was light in color and more difficult to observe compared to the other solutions. Many previous experiments had already shown that gels with no coloring agents were very difficult to observe visually. Control experiments performed without the presence of methylene blue showed that the methylene blue did not affect gel times under these conditions.

A similar experiment was performed using 4 arm NHS polyethylene glycol (molecular weight 10,000) mixed with an equimolar concentration of a multiarm amine-terminated polyethylene glycol (molecular weight 20,000). FD&C Blue #2 dye (indigo carmine) was present in the resultant hydrogel at a concentration of 0.05, 0.1, 0.25, 0.5, 1.0, and 2.5 mg/ml. The hydrogel was applied at a thickness of about 1.0 mm and observed by two independent observers and the ability to observe the gel was rated as adequate or inadequate. The results showed that good visualization of the hydrogel could be obtained at concentrations of at least 0.25 mg/ml FD&C Blue #2.

Example 23

Colorants are Stable in Suitable Solutions

This example was directed to the evaluation of the stability of colorants in solution. An 0.5 mg/ml amount of FD&C BLUE #2 dye (also called indigo carmine) was dissolved in 0.1 M sodium borate decahydrate pH 10 buffer, in deionized water, and in 0.01 M sodium phosphate buffer pH 4.0. Solutions were stored for up to 48 hours at 4° C., 25° C., and 40° C. The dye appeared visually to be stable in solubility and color in the distilled water and phosphate buffer solutions although the dye changed the pH of the phosphate buffer from 4 to 6.9. The dye changed color in the borate solution. FD&C blue #2 and Methylene blue were observed to be not completely soluble so that their concentration is significant. FD&C Blue #2 was soluble at less than 2.5 mg/ml but its maximum solubility was not ascertained.

Example 24

Effects of Coloring Agents on Gelation Times

This experiment was directed to the effect of coloring agents on gelation times. A 4 arm NHS polyethylene glycol (molecular weight 10,000) solution was mixed with an equimolar concentration of a multiarm amine. Both an amine terminated polyethylene glycol (molecular weight 20,000) was evaluated as well as dilysine. Visualization agent was mixed with the buffer used to reconstitute the amine and was present in the resultant hydrogel at a concentration of 12.5 mg/ml. Gel time tests were performed in triplicate. Gel time was measured immediately on reconstitution of the ester (time zero) and 1.5 hours later. The mean gelation times in seconds±standard deviation were: FD&C Blue #1 gelation time 1.57±0.12 time zero compared to 2.2±0.05 after 1.5 hours; FD&C Blue #2 gelation time 1.51±0.12 time zero compared to 2.08±0.09 after 1.5 hours; Methylene Blue gelation time 1.67±0.28 at time zero compared to 1.97±0.12 after 1.5 hours; No visualization agent gelation time 1.39±0.02 compared to 1.78±0.13 after 1.5 hours. These visualization agents did not cause an unacceptable change in gelation times.

Example 25

Synthesis of Succinimidyl Glutarate PEG (SG-PEG)

Figure 16:
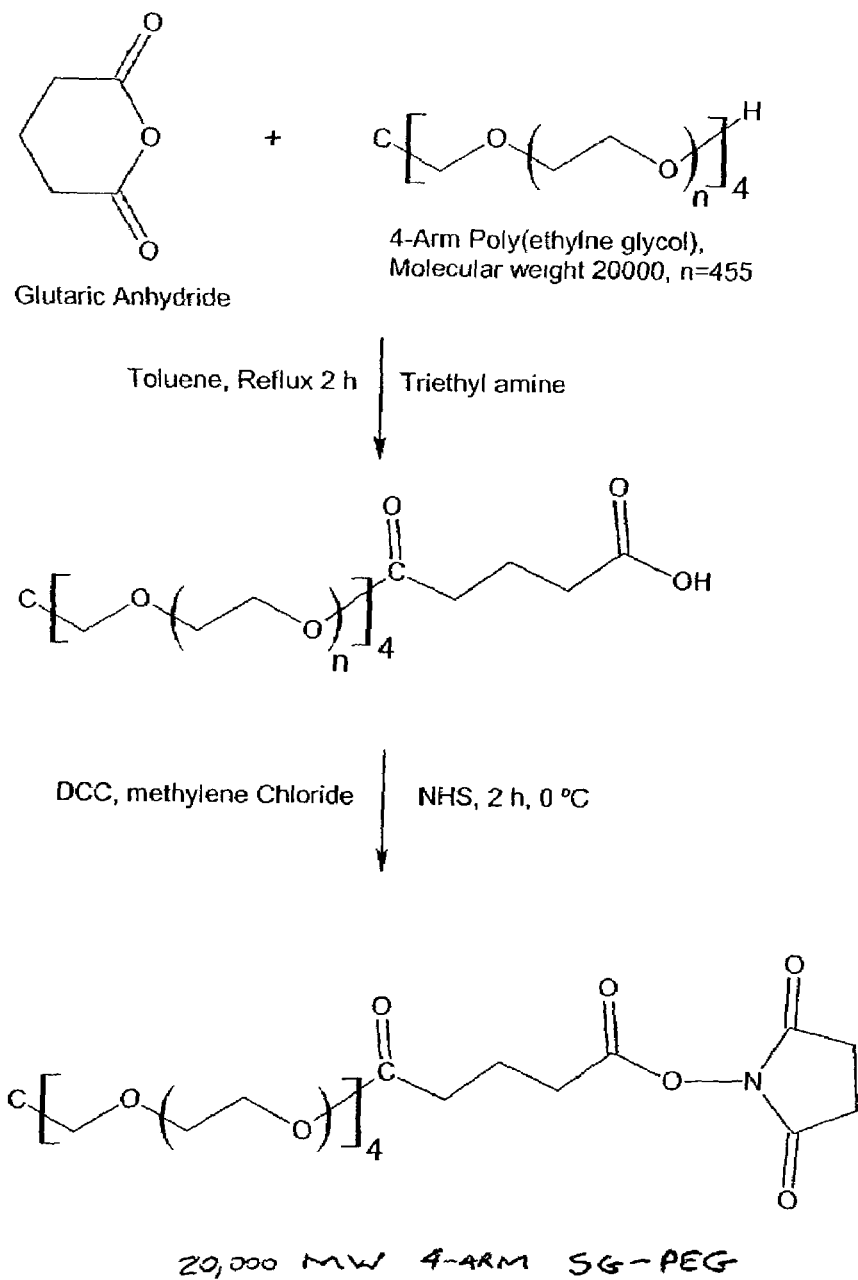
FIG. 16 depicts a method for making 20,000 MW 4 arm succinimidyl glutarate PEG (SG-PEG).

Synthesis of succinimidyl glutarate PEG (SG-PEG). Materials: This Example is written in terms of 4-armed 20,000 MW PEG. A person of ordinary skill in these arts, however, will understand after reading this example how to substitute other PEGs into this procedure, including PEGs of differing molecular weights, and different numbers of arms. 4-Arm PEG-20000 with hydroxyl end groups is purchased from Shearwater Corporation (Catalogue Number 0J0000P04). Alternatively, 4-arm PEG 20000 can be synthesized by ethoxylation of pentaerythritol. This can be done by initiating the polymerization of ethylene oxide using pentaerythritol or other polymer synthesis methods known in the polymer chemistry art. All other reagents and solvents are obtained standard laboratory chemical suppliers such as Aldrich and Fluka. Alternatively, 4-Arm PEG-20000-Tetraglutarate NHS ester can also be purchased from Shearwater Corporation. Reference may be had to U.S. Pat. Nos. 6,437,025 and 5,514,379, hereby incorporated herein by reference, for further direction. See also FIG. 16.

Synthesis a) Preparation of 4-Arm-PEG-20000-tetraglutarate 20 grams of 4-arm PEG-20000 is dried under vacuum at 110° C. or by azeotropic distillation with toluene. 20 grams 4-arm PEG-20000 and 250 ml toluene are added to 500 ml 2-necked reaction flask. 50 ml of toluene is distilled over under nitrogen atmosphere and the reaction mixture is cooled to ambient temperature. To this mixture, 2.28 grams glutaric anhydride and 0.40 grams triethyl amine are added and the mixture is refluxed for 2 hours. The reaction mixture is cooled to room temperature and the PEG-glutarate is precipitated by pouring the reaction mixture into 2 L cold hexane. The precipitate is collected by filtration and is further purified by repeated dissolution and precipitation using toluene-hexane solvent-nonsolvent combination. Finally the purified product is dried under vacuum at 40° C. until constant weight. The PEG-glutarate is immediately used in subsequent reaction given below.

b) Synthesis of n-hydroxysuccinimide Ester of PEG-2000-tetraglutarate 20 grams of PEG-tetraglutarate from pervious synthesis step, 1.0 gram n-hydroxysuccinimide and 100 ml methylene chloride are charged into 500 ml 2-necked reaction flask. After complete dissolution of reactants under nitrogen atmosphere, 0.89 grams of dicyclohexylcarbodiimide (DCC) is added and the solution is stirred for 3 hours and then cooled to 0° C. The dicyclohexylurea, a reaction byproduct, is removed by filtration and the filtrate is evaporated to dryness by rotary evaporation, re-dissolved in a minimal amount of methanol (20 ml) and filtered again. The filtrate is then poured into 2 L cold diethyl ether to precipitate the NHS ester. The ester was purified by repeated dissolution using toluene-hexane solvent-nonsolvent combination. Finally the product is dried under vacuum at 40° C. until constant weight.

Example 26

In Situ Polymerization with a Hydrogel Suitable for MIS Applications

An embodiment of a biocompatible, covalently crosslinked synthetic hydrogel is a hydrogel made using a first precursor that is a four armed carboxymethyl Hydroxybutyrate N-Hydroxysuccinimidyl polyethylene glycol (CM-HBA-NHS) of about 10,000 MW and a second precursor that is a polyethylene glycol molecule of about 20,000 MW having eight arms that each terminate in a primary amine. The first precursor is preferably dissolved in 0.01 M pH 4.0 $NaH_2PO_4$ (monobasic diphosphate). The second precursor is preferably dissolved in 0.1 M $Na_2B_4O_7$ (borate) buffer, pH 9.5. The concentration of precursor in each buffer is preferably about 8.5% solids. The borate buffer preferably includes about 0.5 mg/ml methylene blue dye. The arms on the precursors are preferably about equal in molecular weight. In use, the first and second precursors are dissolved in buffer solution and the buffer solutions are combined in equal volumes. The components are highly suitable for MIS applications and the mixture of the components in situ results in the formation of a tissue-adhesive hydrogel within about 0.5 to about 5 seconds.

Example 27

In Situ Polymerization with a Hydrogel Suitable for MIS Applications

An embodiment of a biocompatible, covalently crosslinked synthetic hydrogel is a hydrogel made using a first precursor that is a 20,000 MW poly(ethylene glycol) succinimidyl glutarate ester and a second precursor that is a trilysine. The first precursor is preferably dissolved in 0.01 M pH 4.0 $NaH_2PO_4$ (monobasic diphosphate). The second precursor is preferably dissolved in 0.1 M $Na_2B_4O_7$ (borate) buffer, pH 9.5. Methylene Blue dye is preferably present in the sodium phosphate buffer solution at a concentration of about 0.5 mg/ml. In use, the first and second precursors are dissolved in a buffer solution and the buffer solutions are combined in equal volumes. The components are highly suitable for MIS applications and the mixture of the components in situ results in the formation of a tissue-adhesive hydrogel within about 0.5 to about 5 seconds.

Example 28

In Situ Polymerization Using an MIS Sprayer with a Hydrogel Suitable for MIS Applications A preferred mode of applying precursors is by spraying, as is set forth, for example, in U.S. Pat. No. 6,179,862 Example 1 and FIGS. 1A-1D, presented herein as FIGS. 15A-15D. Sprayer 2010 of FIGS. 15A-15D is used in conjunction with aqueous solutions of crosslinkable monomers. Solution 1, consisting of a 10% solution of a polyethylene glycol diacrylate (M.W. 3,000 Da, purchased from Shearwater Polymers, Huntsville, Ala.) dissolved in normal saline (pH 5-6) and containing 500 ppm of hydrogen peroxide is drawn up in syringe 2013, preferably a 5 cc syringe. Solution 2, consisting of a 10% solution of a polyethylene glycol diacrylate dissolved in normal saline (pH 5-6) and containing 5000 ppm of ferrous sulfate peroxide, is drawn up in syringe 2014, also a 5 cc syringe. Syringes 2013 and 2014 are individually loaded in compartments 2023, and are coupled to tubes 2024 and 2025 and actuator 2015.

Airflow from a regulated source of compressed air (an air compressor such as those commercially available for airbrushes) is connected to the sprayer 2010 using a piece of tubing. When actuator 2015 is depressed, a steady spray of the two liquid components will be observed. When this spray is directed to a piece of tissue a hydrogel coating will be observed to form on the surface of the tissue. The hydrogel coating is resistant to rinsing and is well adhered to the tissue surface. Within a short period of time (less than a minute) an area of 10 cm×5 cm may be coated with ease.

Example 29

In Situ Polymerization in Humans Using an MIS Sprayer with a Hydrogel Suitable for MIS Applications The materials and methods of Example 27 were used to effectively treat human patients, as described in greater detail in commonly assigned U.S. Provisional Patent Application No. 60/359,236, filed Feb. 20, 2002, entitled "Sprayable Adhesions Barrier", which is hereby incorporated by reference. Patients were enrolled in a clinical study and treated with the materials and methods of Example 26. A spray applicator as described in U.S. Pat. Application No. 6,165,201, hereby incorporated herein by reference, was used to apply the precursors. Other spray applicators, as described elsewhere herein and in U.S. Pat. No. 6,179,862, are also suitable.

Fourteen patients were randomly assigned to have one ovary sprayed with the precursor-derived gel and the other ovary treated with good surgical technique alone. The precursors were applied using minimally invasive laparoscopic surgical techniques. The treated side and the untreated side of the pelvic area were captured on videotape. Randomized patients underwent a second look laparascopy between three and sixteen weeks following the initial procedure. The adhesions in the patients were scored using a blinded third party review of the videotapes. Evaluation parameters included: presence or absence of adhesions; number of adhesion sites; extent of ovarian surface covered by adhesions; severity score; and surface area with adhesions. The treated side had a mean surface area of about 5 cm$^2$ covered by adhesions compared to about 10 cm$^2$ for the control side (p<0.04). These experiments showed that the materials and methods were effective in humans and reduced the risk of patient injury caused by adhesions.

While preferred illustrative embodiments of the invention are described above, it will be apparent to one skilled in the art that various changes and modifications may be made therein without departing from the invention, and it is intended in the appended claims to cover all such changes and modifications which fall within the true spirit and scope of the invention.

What is claimed is:

1. A method of coating a patient's abdominopelvic tissue comprising:
   delivering to the abdominopelvic tissue, using minimally invasive surgical techniques, a first synthetic reactive precursor species and a second reactive precursor species and
   mixing the reactive precursor species to interact with each other to form a biocompatible, covalently crosslinked, synthetic hydrogel in situ within about one minute of the mixing that adheres to the abdominopelvic tissue, is hydrolytically biodegraded, and is effective in humans to reduce the risk of patient injury caused by adhesions,
   wherein the first reactive precursor species comprises nucleophilic functional groups and the second reactive precursor species comprises electrophilic functional groups and the mixing of the reactive precursor species causes the electrophilic functional groups and the nucleophilic functional groups to form covalent bonds with each other to form the hydrogel wherein the hydrogel is hydrolytically biodegraded in less than about 30 days and wherein the reactive precursor species are delivered to the tissue using a spray applicator.

2. A hydrogel composition adapted for use with a tissue of a patient, the composition being made by the process of claim 1.

3. The method of claim 1 wherein the second reactive precursor species further comprises at least two polyethylene oxide repeating groups.

4. The method of claim 1 wherein the hydrogel further comprises a biologically active agent.

5. The method of claim 1 wherein the first reactive precursor species comprises between about 3 and about 8 of the nucleophilic functional groups.

6. The method of claim 1 wherein the second reactive precursor species has a molecular weight between about 5,000 and about 50,000.

7. The method of claim 1 wherein the second reactive precursor species is synthetic.

8. The method of claim 1 wherein the first reactive precursor species consists essentially of dilysine, trilysine, or tetralysine.

9. The method of claim 1 wherein the biocompatible, covalently crosslinked, synthetic hydrogel is formed within about 4 seconds.

10. The method of claim 1 wherein a concentration of the first reactive precursor species and the second reactive precursor species are combined to form a total solids concentration of solids in the hydrogel of about 8 to about 20 percent.

11. The method of claim 1 wherein the hydrolytic biodegradation occurs by degradation of esters.

12. A method of coating a patient's abdominopelvic tissue comprising:

delivering to the abdominopelvic tissue, using minimally invasive surgical techniques, a first synthetic reactive precursor species and a second reactive precursor species and mixing the reactive precursor species to interact with each other to form a biocompatible, covalently crosslinked, synthetic hydrogel in situ within about one minute of the mixing that adheres to the abdominopelvic tissue, is hydrolytically biodegraded, and is effective in humans to reduce the risk of patient injury caused by adhesions, wherein the second reactive precursor species comprises electrophilic functional groups and the mixing of the reactive precursor species causes the electrophilic functional groups to react with nucleophilic functional groups in the first reactive precursor species to form covalent bonds to form the hydrogel, wherein the first reactive species consists essentially of dilysine, trilysine, tetralysine, or a combination thereof and wherein the reactive precursor species are delivered to the tissue using a spray applicator.

13. The method of claim 12 wherein the hydrogel further comprises a biologically active agent.

14. The method of claim 12 wherein the second reactive precursor species has a molecular weight between about 5,000 and about 50,000.

15. The method of claim 12 wherein the hydrogel is hydrolytically biodegraded in less than about 30 days.

16. The method of claim 12 wherein the biocompatible, covalently crosslinked, synthetic hydrogel is formed within about 4 seconds.

17. The method of claim 12 wherein a concentration of the first reactive precursor species and the second reactive precursor species are combined to form a total solids concentration of solids in the hydrogel of about 8 to about 20 percent.

18. The method of claim 12 wherein the hydrolytic biodegradation occurs by degradation of esters.

* * * * *